(12) United States Patent
Hervàs Marin et al.

(10) Patent No.: US 12,123,059 B2
(45) Date of Patent: Oct. 22, 2024

(54) PREDICTING CARDIOTOXICITY RISK IN CANCER PATIENTS RECEIVING ANTHRACYCLINES CHEMOTHERAPY

(71) Applicants: Fundación Para La Investigación Del Hospital Universitario La Fe De La Comunidad Valenciana, Valencia (ES); Maastricht University, Maastricht (NL)

(72) Inventors: David Hervàs Marin, Valencia (ES); Ana Santaballa Beltràn, Valencia (ES); Carmen Salvador Coloma, Valencia (ES); Rubèn Carrero Garcìa, Valencia (ES); Rafael Sanchez Sanchez, Valencia (ES); Akaitz Dorronsoro Gonzàlez, Valencia (ES); Imelda Ontoria Oviedo, Valencia (ES); Sandra Tejedor Gascòn, Valencia (ES); Estaban Peiró Molina, Valencia (ES); Amparo Hernándiz Martinez, Valencia (ES); Hernán González-King, Valencia (ES); María Ciria Calduch, Valencia (ES); Delia Castellano Izquierdo, Valencia (ES); Joaquín Panadero Romero, Valencia (ES); Jose Anastasio Montero Argudo, Valencia (ES); Pilar Sepúlveda Sanchis, Valencia (ES); Nahuel A. García, Valencia (ES); Florian Caiment, Maastricht (NL); Jos Kleinjans, Maastricht (NL); Stephane Heymans, Maastricht (NL); Jort Merken, Maastricht (NL)

(73) Assignees: Fundación Para La Investigación Del Hospital Universitario La Fe De La Comunidad Valenciana, Valencia (ES); Maastricht University, Maastricht (NL)

( * ) Notice: Subject to any disclaimer, the term of this patent is extended or adjusted under 35 U.S.C. 154(b) by 424 days.

(21) Appl. No.: 17/418,725

(22) PCT Filed: Dec. 16, 2019

(86) PCT No.: PCT/EP2019/085388
§ 371 (c)(1),
(2) Date: Jun. 25, 2021

(87) PCT Pub. No.: WO2020/136032
PCT Pub. Date: Jul. 2, 2020

(65) Prior Publication Data
US 2022/0081725 A1    Mar. 17, 2022

(30) Foreign Application Priority Data

Dec. 23, 2018 (EP) .................. 18248213

(51) Int. Cl.
*C12Q 1/6886* (2018.01)
*C12N 15/113* (2010.01)

(52) U.S. Cl.
CPC .......... *C12Q 1/6886* (2013.01); *C12N 15/113* (2013.01); *C12Q 2600/142* (2013.01); *C12Q 2600/178* (2013.01)

(58) Field of Classification Search
CPC ............ C12N 15/113; C12Q 2600/142; C12Q 2600/178
See application file for complete search history.

(56) References Cited

U.S. PATENT DOCUMENTS

2013/0289141 A1*  10/2013  Spinale ................ C12Q 1/6883
                                                          435/6.12

FOREIGN PATENT DOCUMENTS

| DE | 102012101557 A1 * | 8/2013 | ........... C12N 15/111 |
| DE | 102015216782 B3 * | 1/2017 | ........... C12Q 1/6883 |
| WO | WO 2012010905 A2 | 1/2012 | |
| WO | WO 2012010905 A3 | 1/2012 | |
| WO | WO-2016054591 A1 * | 4/2016 | ........... A61K 31/713 |
| WO | WO-2016133395 A1 * | 8/2016 | ........... C12Q 1/6883 |

OTHER PUBLICATIONS

Ruggeri (Heart Fil Rev 2018—pub online Sep. 25, 2017 vol. 23 pp. 109-122).*
Ali Sheikh Md Sayed, Ke Xia, Umme Salma, Tianlun Yang, Jun Peng, Diagnosis, Prognosis and Therapeutic Role of Circulating miRNAs in Cardiovascular Diseases, Heart, Lung and Circulation, vol. 23, Issue 6, 2014, pp. 503-510, ISSN 1443-9506 (Year: 2014).*

(Continued)

*Primary Examiner* — Neil P Hammell
*Assistant Examiner* — Shabana S Meyering
(74) *Attorney, Agent, or Firm* — Daniel A. Blasiole; DeWitt LLP

(57) ABSTRACT

The present invention refers to an in vitro method for predicting cardiotoxicity risk in a cancer patient receiving, or susceptible to receive, anthracyclines chemotherapy based on the determination of the expression levels of a combination of 10 circulating miRNAs consisting of miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p, in a biological sample isolated from the patient. The present invention also refers to said set of 10 circulating miRNAs for its use as biomarker of prediction of cardiotoxicity risk in cancer patients receiving, or susceptible to receive, anthracyclines chemotherapy. Finally, a method for the prevention of cardiotoxicity, in patients receiving or susceptible to receive anthracyclines chemotherapy, that comprises modulating the expression levels of the set of said 10 circulating miRNAS is contemplated.

4 Claims, 20 Drawing Sheets

(56) References Cited

OTHER PUBLICATIONS

Vacchi-Suzzi, C., Bauer, Y., Berridge, B. R., Bongiovanni, S., Gerrish, K., Hamadeh, H. K., Letzkus, M., Lyon, J., Moggs, J., Paules, R. S., Pognan, F., Staedtler, F., Vidgeon-Hart, M. P., Grenet, O., & Couttet, P; Perturbation of microRNAs: rat heart during chronic doxorubicin; PloS one, 7(7), e40395 (Year: 2012).*

Ruggeri, C., Gioffré, S., Chiesa, M., Buzzetti, M., Milano, G., . . . , & D'Alessandra, Y. (2018). A Specific Circulating MicroRNA Cluster is Associated to Late Differential Cardiac Response to Doxorubicin-Induced Cardiotoxicity in Vivo. Disease markers, 8395651 (Year: 2018).*

MicroRNAs as early toxicity signatures of doxorubicin in human-induced pluripotent stem cell-derived cardiomyocytes, Chaudhari, Umesh; Nemade, Harshal; Gaspar, John Antonydas; Hescheler, Juergen; Hengstler, Jan G.; Sachinidis, Agapios; Archives of Toxicology, 90(12), 3087-3098; ISSN: 0340-5761 (Year: 2016).*

Hahn VS, Lenihan DJ, Ky B. Cancer therapy-induced cardiotoxicity: basic mechanisms and potential cardioprotective therapies. J Am Heart Assoc. Apr. 22, 2014;3(2): e000665. doi: 10.1161/JAHA.113.000665. PMID: 24755151; PMCID: PMC4187516 (Year: 2014).*

Rupaimoole, R., Slack, F. MicroRNA therapeutics: towards a new era for the management of cancer and other diseases. Nat Rev Drug Discov 16, 203-222 (2017) (Year: 2017).*

Chiranjib Chakraborty, Ashish Ranjan Sharma, Garima Sharma, C. George Priya Doss, Sang-Soo Lee, Therapeutic miRNA and SIRNA: Moving from Bench to Clinic as Next Generation Medicine, Molecular Therapy—Nucleic Acids, vol. 8, 2017, pp. 132-143, ISSN 2162-2531 (Year: 2017).*

Schultheiss Heinz-Peter, Lassner Dirk, Rohde Maria, Siegismund Christine; DE 102015216782 B3 English Translation (Year: 2015).*

Lasner Dirk, Rhode Maria, Kuehl Uwe, Schultheiss Heinz-Peter; DE 102012101557 A1 English Translation (Year: 2012).*

Chaudhari U, Nemade H, Gaspar JA, Hescheler J, Hengstler JG, Sachinidis A. MicroRNAs as early toxicity signatures of doxorubicin in human-induced pluripotent stem cell-derived cardiomyocytes. Arch Toxicol 2016; 90(12): 3087-98.

International Search Report and Written Opinion. PCT/EP2019/085388. Dec. 16, 2019.

Leger KJ, Leonard D, Nielson D, de Lemos JA, Mammen PP, Winick NJ. Circulating microRNAs: Potential Markers of Cardiotoxicity in Children and Young Adults Treated With Anthracycline Chemotherapy. J Am Heart Assoc 2017; 6(4).

Ruggeri, C., Gioffre, S., Achilli, F., Colombo, G. I., Alessandra, Y. D. Role of microRNAs in doxorubicin-induced cardiotoxicity: an overview of preclinical models and cancer patients. Heart Fail Rev 2018; 23: 109-122.

Song, L., Qiao, G., Xu, Y., Ma, L., Jiang, W. Role of non-coding RNAs in cardiotoxicity of chemotherapy. Surgical Oncology 2013; 27:526-538.

Zhu, H., Han, Z., He, S., Jin, S., Xu, S., Fang, X., Zhang, Y. Specific MicroRNAs comparisons in hypoxia and morphine preconditioning against hypoxia-reoxgenation injury with and without heart failure. Life Sciences 2017; 170: 82-92.

* cited by examiner $$\Pr(Positive) = \frac{e^{-1.228-0.041*miR4732-0.066*miR22-0.02*miR30b+0.081*miR16_{5p}-0.053*miR148a+0.012*miR192-0.009*miR150p-0.055*miR215+0.0899*miR486}}{1+e^{-1.228-0.041*miR4732-0.066*miR22-0.02*miR30b+0.081*miR16_{5p}-0.053*miR148a+0.012*miR192-0.009*miR150p-0.055*miR215+0.0899*miR486}}$$

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| HSNPA | TRMT112 | JUN | CCNE1 | HSPA6 | ERRFI1 | Ncoa2 | DNAH14 | CPM | SYNPO |
| HIST1H4A | KLHL25 | SF1 | HSPA4 | LHX1 | ZCCHC10 | SMARCC2 | NADK | HSPA4 | CPM |
| HSPA4 | HECTD1 | PIH1D1 | GCOM1 | CAMK1 | RNF10 | SMARCC1 | HIST1H4A | MOCS1 | BUB1B |
| HSPA8 | ZRANB1 | POLR3C | SRSF12 | ANXA2P2 | NCBP1 | ACTG1 | FTSJ2 | MFAP3 | SSFA2 |
| P4HA1 | ERBB2IP | POLR3A | DYNLL1 | PPHLN1 | CRKL | RB1 | TRIM14 | SQLE | SEC23IP |
| MFAP3 | HSPA5 | PFDN6 | ATPIF1 | WDR5 | HSPA9 | NELFB | ZRANB3 | DLG1 | UBAC1 |
| LEMD3 | NRCAM | SMIM21 | DLG1 | CTNNAL1 | HSPA8 | ZNF70 | UBE2QL1 | C11orf30 | DBN1 |
| DLG1 | GLRX3 | ANAPC16 | DLG3 | C2CD5 | HIPK3 | FBXO11 | PLK1 | RMND5A | HAUS1 |
| ZNF703 | IKBKB | DIAPH2 | DLG2 | WIPI2 | B2M | BUD31 | HIGD1A | ALOXE3 | LGALS1 |
| FAM114A1 | AKT1 | CREB5 | DLG4 | NUP93 | MFAP4 | PPARGC1A | NDUFB5 | BCAT1 | SMG5 |
| ZMYM6 | RBM4B | KRTAP3-2 | RPF2 | STK3 | SRSF10 | RPS4X | BBX | MTUS2 | SMG7 |
| NUP98 | PKP4 | AIF1L | LOC101060521 | ZNF175 | MFAP1 | E2F1 | TRMT61A | TNNT2 | DLG2 |
| MUC1 | NOSTRIN | MTUS2 | TAZ | ERI3 | SRSF12 | JPH1 | FTSJ3 | MON2 | DLG4 |
| ELOVL1 | IKBKG | ATP2B2 | NOB1 | CEP70 | DBN1 | AFF1 | SETD1A | KCNJ6 | OARD1 |
| PRR14 | KIFAP3 | CSNK2A1 | ESPL1 | CTBP1 | AGT | PPWD1 | LRFN1 | AKAP3 | ZNF703 |
| ZNF775 | UBAC1 | URI1 | SV2C | TNKS | ATP6V1B2 | ZNF24 | NGDN | MBTD1 | TPM4 |
| HSD17B12 | TMEM177 | KRTAP10-9 | CBLC | ATP6V1A | MVB12A | ZNF71 | ZNF512 | CEP70 | TNNT2 |
| CAPZB | AL645728.1 | KRTAP10-8 | ARHGEF11 | LMO4 | HSPA5 | TARSL2 | SRSF12 | ATMIN | ALMS1 |
| FBXW11 | NDUFAB1 | CD3EAP | CAMK2D | NOP2 | LARP1 | LDOC1 | S100A13 | ZSCAN12 | GRWD1 |
| RPS27L | SNRNP200 | KRTAP10-5 | MUC1 | POLR1D | PIK3CA | LRPPRC | RASAL2 | TNFSF13 | PRIM1 |
| ATP2A3 | DLG3 | KRTAP10-3 | SP7 | STIP1 | PIK3CB | RARA | DEPDC1B | TNFSF12 | OFD1 |
| TNNT2 | DKK3 | KRTAP10-1 | IQCG | TNNT2 | NAPG | FTSJ3 | USP21 | ACTA1 | METTL17 |
| SFXN3 | NFE2L2 | KRTAP10-7 | CSF3R | APOB | CRBN | ZNF384 | MOAP1 | EVL | WDR1 |
| SFXN1 | SMARCB1 | APP | LRP6 | WDR47 | ZC3H14 | ZNF354A | GNL2 | ANO4 | ARHGEF17 |
| SWAP70 | MAP3K7 | HIRIP3 | RSU1 | WDR48 | OLIG1 | HIST1H1A | EP300 | UBE2D2 | SRFBP1 |
| XPO1 | PPP2R4 | RPL8 | GATA3 | LNX1 | VAC14 | BHLHE40 | ZNF354A | ITGA7 | SRP14 |
| XPO7 | NAV1 | RPL9 | POLR3F | EFTUD2 | DHX8 | BHLHE41 | RBPJ | IMPAD1 | IL2RB |
| GTF2B | GOLGA2 | KAT2B | UBE4A | ZIC2 | CBLB | THRB | CPT2 | GABBR1 | CAMK2B |
| MAPK1IP1L | DLGAP1 | POLR1A | POLR3G | HOXB9 | ATP8 | DCC | DDX31 | CHKA | CEP89 |
| PDLIM1 | UBR5 | POLR1B | CCND1 | HOXB6 | ZMYM6 | ZFP2 | CBFA2T2 | UFSP2 | FXR2 |
| HIST2H3C | CDK9 | POLR1C | TPI1 | HIST2H3A | DIAPH1 | CRNKL1 | PCF11 | XPO4 | ABLIM1 |
| GART | MALT1 | POLR1D | ACLY | ARL5B | WDR1 | HSP90AB1 | ANKMY1 | MRFAP1L1 | CEP83 |
| ING1 | NUP214 | POLR1E | YBX1 | ATAD5 | MUC1 | GOLGA2 | FAM110B | EPPK1 | MUC13 |
| ANAPC7 | MAPRE1 | NCKAP5L | YBX3 | TOP1 | PPP2R2A | DKC1 | ZC3HAV1 | DMAP1 | GTF2F1 |
| RPS6KA5 | SETDB1 | RUVBL1 | UBE2D2 | APITD1 | AGER | CDH1 | P3H1 | KSR1 | AKAP2 |
| ZC3H3 | MAPRE2 | XPO7 | UBE2D3 | KRT17 | PIK3CB | sep-14 | DYRK1A | GTF2I | ZNF174 |
| PSMD10 | ENTPD6 | RUVBL2 | UBE2D1 | FLNB | GC | CDH3 | C3orf17 | TSPYL4 | WHSC1 |
| IL15RA | HMGA1 | BACH1 | POLR1A | FLNC | CSF3R | KDM2B | DYRK1B | CCDC57 | GTSE1 |
| KLHL22 | MRPL35 | KRTAP4-2 | POLR1B | EIF4A1 | COX6A1 | sep-11 | ZFP62 | AKTIP | DDX47 |
| SMAD6 | TAP1 | KRTAP9-4 | POLR1C | ANKRA2 | FAM172A | sep-10 | ZMYM2 | ING3 | GADD45GIP1 |
| GOLPH3L | NUP98 | CCT4 | POLR1D | EIF4A3 | WDTC1 | SF3A1 | ZMYND8 | ATAD1 | PRR14 |
| VAPB | MFI2 | KBTBD8 | XPO1 | EIF4A2 | MAX | ZMYM2 | TBC1D25 | ITGAV | LAT |
| VAPA | KRT23 | ZBTB34 | TANK | SMS | SRSF8 | CENPN | FNTB | KIAA1377 | ZNF281 |
| DCTN2 | MUC1 | SIRT7 | ZNF454 | VAPA | ARHGAP12 | DDIT3 | CAMK2D | GOSR1 | ACTA2 |
| DCTN1 | TRIM27 | EFEMP2 | SOX10 | SMAD3 | CSN2 | CENPK | PRRC2B | INA | CAPZB |
| NCOA1 | TRIM21 | KRTAP10-11 | MRPL17 | DCTN2 | LAT | POTEI | PRRC2A | SDCCAG8 | ACTA1 |
| ACAT1 | COG5 | POLR2E | EFTUD2 | DCTN3 | PAIP2B | CENPI | CAMK2G | SLC2A14 | RRP1B |
| DDB1 | COG4 | ASTN2 | ISG15 | PLP2 | CCDC114 | TPM3 | CLCN7 | VAPB | MYO18A |
| LONRF2 | USP39 | POLR2F | WSB1 | DCTN1 | TSG101 | TRIM24 | CAMK2A | VAPA | DYNC1I2 |
| CTNNB1 | CGNL1 | POLR2L | TBC1D25 | GPRC5A | FKBP2 | SP1 | TRIM22 | LINC00852 | HIP1R |
| CAPZA1 | NUPL1 | POLR2H | VTA1 | RL2 | RPS27A | MGP | IWS1 | EVPL | ARNTL |
| WASL | NUPL2 | ANAPC7 | EEF2K | FAM74A4 | MYO18A | TRIM27 | PJA1 | TRIM55 | CCT8 |
| RCVRN | HBB | SUPT6H | FUNDC1 | SMC3 | POLR1D | PRMT6 | FXR2 | DCTN6 | BMS1 |
| BAD | CSNK2A1 | CDC27 | ZNF227 | ACTR10 | RNPS1 | RPL17 | ANKRD34A | TNFSF13B | APOB |
| ERH | ARID5B | CDC26 | SENP3 | RAD51AP1 | XPO1 | BRD8 | MUC19 | NEDD8 | MRPL16 |
| HIST2H4A | FDPS | RBPMS | GARS | S100A9 | CCT8 | RFC3 | CCDC155 | RBM12 | CCT2 |
| UBTF | DNAJA1 | SHISA6 | ZNF878 | RBM14 | WDR44 | RPL13 | BRD4 | BEND7 | CCT3 |
| IMPDH1 | PTGES3 | PDRG1 | POLR2E | S100A6 | XPO7 | BRD4 | GPATCH4 | Ube2g2 | SOX13 |
| ACAA2 | KIF5B | MYBBP1A | KCNH1 | TNKS1BP1 | CCT2 | COPS3 | GIGYF1 | LRIG3 | CCT7 |
| POTEI | AKT2 | MYH15 | CAMSAP3 | UBE2V2 | CCT3 | CENPU | AARS2 | NOL6 | UACA |
| ILVBL | DDX47 | SPRY2 | PPP1R2 | SCAF8 | PIKFYVE | EIF2B1 | TESK2 | ABT1 | CCT5 |
| TIMM50 | TRA2A | SPRY1 | CBL | CMBL | CCT7 | ZAK | KCTD13 | A2ML1 | JAK3 |
| GFAP | MICAL3 | NOTCH2NL | RASAL2 | GOLGA8EP | CCT4 | ZNF445 | SYNCRIP | CRTAP | JAK1 |
| KPNB1 | IPP | MGAT5B | FRAT1 | NAA30 | CCT5 | ZYG11B | VAT1 | IPO11 | ZNF512 |
| KRT40 | CHTF8 | POLR2K | FRAT2 | LEO1 | EPPK1 | NVL | YWHAZ | MORC4 | CCDC50 |
| MCFD2 | TMEM14B | GPN1 | ZNF350 | RBM6 | JAK2 | MYL12A | TAF12 | ACTR10 | TBC1D2B |
| ENDOD1 | APC | RANBP3 | ATXN3 | PSMD9 | JAK1 | KRTAP10-8 | PPP2CA | ZNF496 | XPOT |
| ANKFY1 | UQCRFS1 | KRTAP5-6 | EIF4A3 | LAPTM4B | BRCC3 | SIN3B | WHSC1 | PLCG1 | TPRN |

FIG. 5A

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| BTRC | APP | PFDN2 | ABHD17B | SGMS2 | TMEM128 | APP | APP | GPATCH2L | DST |
| Mpp6 | IL24 | RIMBP3 | MAP3K1 | WDR82 | EPS15L1 | MAZ | CAMK2B | H3F3A | QRFPR |
| FAS | TNKS | CARS | GIGYF1 | WDR1 | PPARA | RBBP7 | ZNF845 | PPFIA1 | DSP |
| RPN1 | RASGRP3 | JUND | TLE1 | IFT81 | WDR77 | EIF2A | NINL | SKA1 | ANAPC5 |
| RPN2 | POM121C | TAF1C | VAPB | DYNC1I1 | RPRD2 | RBBP4 | POP1 | DYM | CIZ1 |
| SF1 | REL | TAF1B | SMAD3 | NUDC | C21orf58 | NR1I3 | PLEKHA7 | ZMYND19 | ATAD5 |
| IKBKB | DIRAS3 | ZNRD1 | XIAP | RAI1 | FTL | ARHGAP17 | CEP70 | ITGB1 | DZANK1 |
| RASAL1 | RPL9 | HIRA | ANKRD32 | YLPM1 | TNK2 | DDX6 | LIMA1 | HEATR1 | WDR34 |
| MARCH9 | MED21 | WDR92 | AKAP11 | FIP1L1 | PREPL | CEP70 | SURF6 | KPNB1 | WDR36 |
| EGF | PNISR | RPL10A | DCTN3 | CNOT7 | SMYD5 | RNF8 | LZTR1 | KRT40 | WDFY3 |
| CTSS | SNX9 | MYO9A | TSC2 | CNOT6 | SH3D19 | NR1I2 | CPS1 | IL37 | FLOT1 |
| CDCA3 | MACF1 | CSNK2B | TSC1 | KYNU | PSMD14 | GRIP1 | GLYR1 | THAP1 | PDE6D |
| RAN | KHDRBS1 | SSRP1 | BRIX1 | HIST4H4 | PSMD11 | EIF5A2 | ZNF771 | EIF4E2 | MYBBP1A |
| ANKRD13A | FAM98A | EEF1A1 | CIITA | FGFR1OP | CBL | TAF5L | SIRT3 | HAP1 | RRP12 |
| PLEKHH3 | HOXC6 | EEF1A2 | PLRG1 | TYMSOS | APOH | SARS | DTL | HMBOX1 | FLNA |
| GMCL1 | SPECC1L | TFF1 | SAP30BP | EIF4E3 | KRT17 | CTCF | RRP8 | ARSK | FLNB |
| FADD | ST14 | TNNT2 | RBM14 | TBL1X | KRT16 | ATXN2L | SPTAN1 | ZNF398 | FLNC |
| RELA | WIF1 | RPAP3 | NAT9 | TBC1D23 | KRT15 | TNKS | RPL4 | MAP3K15 | MYH10 |
| UQCRFS1P1 | SFXN2 | KIAA1522 | BEND3 | ACTR1A | KRT14 | BATF | FUBP3 | WDR73 | MPP7 |
| TPR | KIF23 | SMARCA5 | H2-Aa | EWSR1 | WDFY3 | MESDC2 | DCLK1 | SERPINA12 | SHROOM3 |
| SNAI1 | BAZ2A | NOP58 | RXRA | SPRED1 | GIT1 | VDR | ZCCHC9 | TGM5 | KIAA0586 |
| RNF19A | NCKAP5 | UBTF | PRKAR1A | SF1 | SERBP1 | SNX7 | PUM2 | NAP1L5 | XIAP |
| ZC3H11A | XRCC2 | CCT6B | LMO4 | PRPF8 | POLR2A | CTNND1 | SFXN3 | IKBKB | PSMD9 |
| APP | AP2B1 | SUPT16H | GEMIN4 | PKP1 | KRT19 | SNX5 | IFNGR2 | MARCH6 | TRIM56 |
| SFN | STARD7 | AC138655.1 | CUL3 | NUDT21 | KRT18 | ZNF184 | TOMM22 | RCBTB2 | GPRC5A |
| UQCRFS1 | NCKAP5L | KRT40 | IFIH1 | PRPF6 | MYH11 | COPS2 | DHX30 | GMCL1 | NCOA1 |
| MMAB | XPO1 | RRN3 | KRBA1 | EIF3M | SNIP1 | TRIM32 | KAT7 | MKLN1 | NCOA6 |
| UQCRC2 | PPM1E | TRIP10 | MDH1 | DDX39A | PAG1 | ACTA2 | JADE3 | HMG20A | TFPT |
| DDAH2 | SRSF6 | KRTAP4-12 | EEF1A1 | EIF3A | RET | RPL5 | JADE2 | PXYLP1 | ELMSAN1 |
| YTHDF3 | TANK | ACTN3 | CTNNB1 | EIF3B | MKRN1 | TRIM37 | JADE1 | PLBD1 | RBM19 |
| YTHDF1 | SRSF3 | ACTN1 | Lzts2 | EIF3C | AUNIP | SUDS3 | KANSL3 | ARRDC3 | TCEA2 |
| NEK4 | ZNF454 | ADAMTSL4 | Zbed3 | EIF3D | REL | RC3H1 | TNNT2 | APP | GRIPAP1 |
| NEK1 | TUBA1C | ACTN4 | VPS25 | EIF3E | DCTN2 | EDC3 | C21orf2 | SLC2A3 | PRKAR1B |
| DDX56 | TCTN3 | TSGA10 | GJB5 | DYNLT3 | RECQL5 | MED1 | RPL7A | YEATS4 | NOL6 |
| RRBP1 | U2AF2 | SIGLEC8 | RAI1 | ZNF264 | DCTN1 | sep-09 | EBNA1BP2 | ACTB | CAPZA2 |
| C11orf54 | SRSF9 | TWISTNB | KLF5 | MTMR4 | TSC2 | DENND4A | NEK1 | NUP85 | CAPZA1 |
| DLD | ECH1 | ATF7 | KLF2 | CENPO | CDC6 | TNNT2 | DDX52 | SMARCE1 | TRIOBP |
| DLAT | JUP | KRTAP9-2 | DEFA1 | CENPN | YTHDC1 | DCP1A | SRGAP2 | RUVBL1 | MPRIP |
| NLRP3 | C4A | ATF2 | SIPA1L1 | CENPM | TNNT2 | RPL36AL | JUN | RUVBL2 | TP73 |
| CREBBP | CSTF1 | | EXTL3 | HPCAL1 | PLRG1 | sep-05 | ZBTB8A | ZBTB8A | LMO7 |
| HDAC1 | SNX33 | | IPO9 | CENPK | SLC36A1 | HHT1 | TPRN | NCAPG | PINX1 |
| ANKRD13D | KLHL8 | | KRT40 | CENPI | ALAS2 | ARID4B | PDPR | TUBB2A | CDC27 |
| HSP90AA4P | CHEK1 | | FBN3 | CENPH | S100A9 | PNMA5 | SAMD1 | MRFAP1 | RPS10P5 |
| CLOCK | TCF4 | | IL33 | CENPC | S100A8 | ADRBK1 | RBMX2 | CEP170 | CDK5RAP2 |
| NLRP9 | RABL6 | | PLEKHO1 | LDB1 | DDB1 | SAP130 | SURF1 | CALML3 | MYL6B |
| UBL4A | POM121 | | IGHM | TPR | STK32C | TIMM8B | FKBP1B | TRIM8 | MORC3 |
| MYO3B | RCN2 | | CPVL | CNOT2 | RIF1 | ARNTL | FNDC3B | HDAC1 | CTTN |
| AKR1C4 | PDLIM2 | | PARD3 | SH3BGRL | C17orf85 | SDHAF1 | PRPF6 | TMEM131 | KRBA1 |
| AKR1C1 | TOMM7 | | SLC35F1 | CENPU | SS18 | SAP30 | TOP2B | STXBP4 | ACTBL2 |
| AKR1C2 | MRPL18 | | BTRC | CENPT | PRKAR1A | IL7 | HNMT | FANCD2 | CDC23 |
| AKR1C3 | DST | | MAP3K11 | CENPQ | SH2B1 | CHD9 | GAR1 | LINC00346 | HMGB1 |
| SET | CHUK | | KIF13B | CENPP | LTK | ZNF75A | TTC5 | ZBTB10 | PLCG1 |
| NOTCH2NL | SENP1 | | EWSR1 | ZC3H11A | SRPK2 | FOS | MRPL11 | SKP2 | MAZ |
| SKP1 | PRKAR1A | | BZW2 | ARID1B | ALK | JUN | DDX56 | RACGAP1 | EPS8 |
| CDT1 | ZNF24 | | ZFPM1 | APP | LMO2 | CAP1 | TTC1 | TPM2 | AFAP1 |
| WDR26 | ACY1 | | LINS | IBA57 | WASL | CAP2 | TICAM1 | WDR26 | OIP5 |
| WDR24 | VHL | | MARCH5 | UQCRFS1 | RADIL | JUP | EFEMP1 | RANBP6 | EPS15 |
| MAPK1 | CTBP1 | | PTK2B | YIPF2 | CDC40 | ZNF318 | KIF18A | CST6 | CDK19 |
| RANBP3 | SLC26A8 | | IKBKG | TMEM43 | CDC42 | HTRA2 | SENP5 | SSX2IP | MAD1L1 |
| CARS | ING5 | | USP28 | YIPF6 | CTTN | PIK3R1 | EFEMP2 | SAAL1 | ATP13A2 |
| SUMO1P1 | PHLDB2 | | ARL2BP | CD2BP2 | WDR6 | NR1H4 | CDK11B | TFIP11 | CDCA2 |
| SATB2 | STRN3 | | PRPF4 | SNX5 | EGFR | BRMS1 | COL4A5 | SMEK1 | ST5 |
| EP300 | EPAS1 | | USP21 | ZNHIT2 | RBPMS | MGEA5 | HIST2H3C | RAD51 | CLIP1 |
| Mpp2 | DAPK2 | | USP20 | ZNF691 | PLCG1 | BAHCC1 | ING4 | SRCAP | SPTBN1 |
| ERCC2 | RBFOX2 | | NFE2L3 | COPS6 | OSGEP | NR1H2 | ING5 | PHF12 | RPGRIP1L |
| EZH2 | TAF1 | | NFE2L2 | DHX38 | AHSG | NR1H3 | PWP2 | USP4 | SIPA1L3 |
| NR1D1 | VAV1 | | NFE2L1 | CCAR2 | LARS2 | RPL18A | CAPG | CEP57L1 | SIPA1L2 |
| NR1D2 | ATP5C1 | | ARHGEF2 | ADAR | CPSF3 | TCF4 | CBY1 | IQGAP1 | PSMC4 |
| SMARCA4 | CBL | | STRAP | C11orf58 | CAD | KPNB1 | NUFIP1 | ASAH1 | PSMC5 |

FIG. 5B

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| UIMC1 | WIZ | | DOCK7 | PKM | EPS15 | DPYSL2 | ZNF701 | RB1 | TTLL6 |
| YWHAZ | NUP153 | | CDH1 | CNOT11 | SIRPA | ACTB | TAF5 | APOA1 | CD44 |
| UNC119 | CSNK1E | | RELB | IBTK | VPS28 | STAT6 | CCDC137 | AMD1 | KPNB1 |
| ABCB7 | KRT15 | | RELA | EIF4H | SRRT | KRT40 | TP53 | ZBTB9 | VPS53 |
| DNAJC11 | KRT14 | | CENPB | AGMAT | AARSD1 | VPS52 | RBFOX2 | FAM207A | LCP2 |
| C3orf38 | EIF4EBP1 | | WDR47 | EIF4E | IMPDH2 | SAP30L | RPL15 | TANC2 | E2F7 |
| INTS6 | STRN | | SNAI2 | EIF4B | YLPM1 | UNC5D | PLSCR1 | CYTH1 | EXOC3 |
| PNN | FLNA | | SNAI1 | MGA | ETNK1 | IGFBP3 | ELP3 | CYTH3 | EIF4E2 |
| VCP | CD2AP | | TESK2 | CALML3 | APCS | DPH2 | FCF1 | HBA2 | TBL1X |
| HIST1H3E | LCK | | RBM45 | TTC19 | PSMC2 | POLR2A | MOK | PBX2 | MYO6 |
| HSPH1 | KRT19 | | DBI | CALML5 | HSD17B4 | PPARA | BTD | PBX3 | C9orf156 |
| TOPBP1 | AGFG1 | | Arhgef11 | MEF2B | TRA2A | EIF4E | HIST1H3A | PBX1 | KIF13B |
| UFD1L | MYH10 | | APP | MEF2A | TRA2B | PWP2 | POLE3 | CHST12 | TNNI2 |
| TIMM44 | MYH11 | | CSAD | PROSC | C21orf91 | NUFIP2 | UTP23 | MEAF6 | WDR76 |
| ACTG1 | RASIP1 | | VIM | HDAC1 | DDX17 | TRIP4 | RPL7L1 | TYMP | UBTF |
| PODXL | TMEM126A | | MRPL40 | ACTA2 | SPATA2L | ING2 | MYBBP1A | TWISTNB | TRIM15 |
| Magi1 | GIGYF2 | | GAA | HDAC3 | KPNB1 | sina | RRP12 | VTI1B | HUWE1 |
| CWC22 | BAG5 | | APC | MYH9 | KRT40 | UBE2I | HERC5 | ZSCAN32 | PES1 |
| TOMM7 | KIAA1467 | | UQCRFS1 | HDAC4 | HGS | EDA2R | TRIM3 | ACTG1 | DAB2 |
| CERS2 | NEB | | XPNPEP1 | HDAC9 | LGALS3BP | ATG2B | ARHGEF26 | TGM1 | GNL2 |
| DNMT1 | ICOSLG | | SPTAN1 | FANCD2 | LCP2 | RELA | RPF2 | RRP7A | Nme2 |
| RORC | NDUFAF5 | | ATP5B | ZBTB10 | SNW1 | RPS6KA4 | RBM28 | RANBP10 | PSMB10 |
| NXPE3 | EIF4E | | COX6B1 | NOTCH2NL | NCK1 | NCOA4 | MCM2 | ZNF382 | DYNLT1 |
| MAGI1 | ATP6V0A1 | | VANGL2 | DNAJB1 | CFH | RNASEH2C | HDAC1 | GSDMA | GNG12 |
| NUP214 | AKAP13 | | DHX34 | H1FX | OGT | PPARG | KDM1A | DNMT1 | BRD2 |
| CUL1 | KRT5 | | DHX35 | DNAJB5 | TFG | AP1G2 | HDAC2 | MAP3K6 | BRD3 |
| CUL2 | FRMD5 | | DHX36 | DNAJB4 | HEXB | Cap1 | BAG6 | MAP3K5 | NOL10 |
| CUL3 | AMER1 | | DDX58 | ETF1 | NCL | POP1 | HDAC4 | ZNF479 | CENPC |
| CCDC77 | CTH | | LCE1E | RANBP3 | CREBBP | FAM195A | UBL4A | ZNF473 | SSH2 |
| PRMT3 | ATP5E | | KHSRP | PATL1 | PNN | MCM4 | BRD1 | CUL1 | CDCA8 |
| PRMT6 | EOGT | | SF3A1 | KLHL11 | SAE1 | ZBTB24 | SDCBP | LUC7L2 | IL2RG |
| CREB1 | STRN4 | | SF3A2 | KRTAP5-6 | PPP3CA | BATF2 | SH3BP4 | BRCA1 | PXDC1 |
| SLC25A20 | HBA2 | | MGEA5 | PODXL2 | GUCA1B | BATF3 | STOM | HLA-DPB1 | ZNF280C |
| MIF | FBXO30 | | SH3BP4 | SDIM1 | SLC1A2 | PCM1 | XIAP | PRMT8 | RP6-24A23.6 |
| DNAJA3 | SRSF7 | | Nono | DLL3 | RBM45 | TTC38 | DARS2 | BRCA2 | RABGAP1L |
| ZAK | RACGAP1 | | UBE2E1 | HAP1 | GHR | ATXN2 | UPF1 | HAL | MRPL47 |
| KPNA5 | TELO2 | | UBE2E3 | C11orf87 | CBR1 | MCM2 | MTIF2 | ANKS6 | MRPL46 |
| KPNA1 | SMC3 | | LRFN1 | KIF1B | NEFH | HDAC1 | NVL | PRMT1 | YEATS4 |
| MYO5C | CCL5 | | SMYD2 | PIP5K1C | DAB2 | KDM1A | GMNN | LRRC1 | DIXDC1 |
| CARM1 | NAV3 | | LARS | LENG1 | PRPF3 | HDAC3 | VDAC2 | BRD8 | APC |
| HIF1A | BCL10 | | TRIM9 | MCMBP | SLC25A13 | HDAC2 | VDAC1 | FGFR2 | ACTB |
| ARHGAP1 | NAV2 | | TRIM8 | LAGE3 | CUL4B | HDAC4 | MTG1 | CTSV | MRPL48 |
| PPM1G | RANBP9 | | VPS51 | RABGAP1 | SIX5 | CLOCK | DDX27 | KAT8 | PAK1 |
| USP48 | HNRNPM | | WDYHV1 | FAM188B | ARHGEF5 | ACTA1 | CDC6 | BRK1 | RPL37A |
| UBAP2L | MARK2 | | TRIM5 | MGLL | MRFAP1L1 | EIF1AX | CDIPT | MORN2 | SPTAN1 |
| KRTAP4-2 | HNRNPAB | | NIF3L1 | SF3B3 | RARS | EIF2B4 | TNPO2 | RBBP7 | MED1 |
| SYT12 | TRAPPC11 | | NUDCD3 | NFYB | MIPEP | ZNF22 | LRIF1 | KAT5 | MED6 |
| UGP2 | ZNF106 | | HDAC4 | ITGB3BP | CCDC12 | EIF2B2 | EHMT2 | TTC17 | MED7 |
| PJA2 | ND4 | | RPLP1 | SMARCA4 | RELA | SDCCAG3 | ALAS1 | PRRX1 | MED4 |
| B4GALT5 | RANBP2 | | PRKAR2A | RAD54B | NCKIPSD | SMAD2 | ZNF624 | ZBTB21 | ARFGAP1 |
| SULT1C3 | RPS27 | | CFAP20 | ATG16L1 | ACIN1 | EIF3E | NEDD1 | DOCK7 | MED8 |
| POM121 | ICOS | | FASTKD5 | PFKP | LPP | TBX2 | CDT1 | C4orf27 | MED9 |
| TUBB6 | LAMA3 | | SNCAIP | HSPD1 | CNOT1 | RPS6 | FAM53C | TNFRSF17 | AP2B1 |
| GBP7 | LAMA4 | | PSEN1 | NFKBIL1 | SNRPD2 | RPS10 | PSMA3 | FAM184A | NCKAP5L |
| GBP6 | SIAH1 | | SNRPA1 | C3orf38 | SYNCRIP | MCRS1 | R3HCC1 | MEIS2 | GTF2E1 |
| PDP1 | KIAA1328 | | ADAP1 | YWHAE | FN1 | ZBTB8A | SIPA1 | MEIS1 | BMF |
| CSE1L | FAM214A | | TPBGL | CASC5 | GFAP | AHNAK | PDCD6 | JUP | SUB1 |
| ASPSCR1 | IL7R | | CST6 | DDX23 | APP | PLRG1 | REEP3 | RNF138 | DDX50 |
| PPP2R5C | PKP2 | | UFM1 | DPH1 | DOCK5 | NPLOC4 | DSG1 | PGK2 | FTSJ3 |
| BAG6 | TFF1 | | Prune | DPH2 | VIM | IKZF1 | KIF21A | GID4 | CBX2 |
| ASNA1 | MTOR | | LRSAM1 | TRIM56 | ECHS1 | NCOR1 | MORF4L2 | EPN1 | RAB11A |
| ILK | EXPH5 | | RRS1 | CACNG1 | UBA52 | PNRC1 | DIDO1 | GID8 | TAB1 |
| KIAA0101 | SND1 | | DOCK6 | NDUFB9 | CYLD | NCOA2 | FBXW7 | TRRAP | C6orf141 |
| HARS | BBX | | GAPDH | PODXL | TUBB4B | NCOA3 | MVP | MB21D2 | PLCH1 |
| POFUT1 | SAV1 | | AGAP1 | PPIL2 | ACTB | NCOA1 | NOP2 | KPRP | PPP1R9B |
| SEC23A | SYNE1 | | SNW1 | PPIL4 | SPTY2D1 | NCOA6 | MAGI1 | SPICE1 | PKN3 |
| CAST | RAD51D | | MTOR | POLR3C | STRADB | ZBTB16 | MYEF2 | PKNOX1 | GCA |
| PSMA1 | NT5DC2 | | JOSD1 | SNRNP200 | STARD10 | STAT1 | NSA2 | PKNOX2 | BUB1 |
| VCPIP1 | NT5DC3 | | KIF1C | DCD | FRS2 | DDX31 | ZNF668 | PALB2 | BUB3 |

FIG. 5C

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| DUS3L | FHOD1 |  | YOD1 | NUP214 | FUS | GPR22 | KIAA0020 | CDC14A | C9orf43 |
| PUS10 | SRSF1 |  | MFN2 | TAGLN2 | FUBP1 | NR2F6 | DDX21 | MDFI | SHB |
| CTDSP2 | SHCBP1 |  | MFN1 | ISL2 | KHDRBS1 | NEDD4 | SYDE1 | MSH6 | UHRF1BP1L |
| PDHA1 | NUP54 |  | ISY1 | PRPSAP1 | AP2B1 | SNRPA1 | AGAP1 | FBXO2 | RNF214 |
| ZC3HAV1L | RSRC1 |  | XAB2 | TRIM29 | RUVBL1 | MAPK3 | SPATA24 | C1orf43 | PHLDB3 |
| OCLN | ATP6V1E1 |  | KIAA1191 | USP39 | ZBTB7B | GTF2A1L | UNG | RPS2 | ZBTB20 |
| NT5DC2 | ACTL8 |  | ACSBG1 | MDM2 | FLT3 | MAPK1 | RPS4X | CDSN | RNASEH2A |
| NT5DC3 | SMU1 |  | USP8 | SETD5 | VASP | FOSL1 | USMG5 | HSDL1 | CALML3 |
| AGXT | BCL7B |  | PTK2 | RPL19 | FIG4 | PAK4 | ALG13 | STAT3 | PPP5C |
| FARSB | FAM83B |  | UBE3A | SNRPD2 | SF3A1 | PSMA5 | Act5C | MARK2 | FCF1 |
| SIGMAR1 | SLC3A2 |  | USP2 | SNRPD1 | PRR22 | FASN | NAT10 | FAM160B1 | KDM3B |
| TTF2 | NME2P1 |  | SF3B1 | CNN2 | RSAD1 | PATL1 | NOP14 | BRAF | VPS51 |
| MAP7 | STX18 |  | SF3B3 | RNF185 | RP11-169F17.1 | BEND7 | STAU1 | ALOX12B | RALA |
| HIST2H2BE | RAPGEF2 |  | USP7 | PTPN11 | Shc1 | RPS24 | ZFYVE21 | MORF4L2 | SSB |
| MID2 | CSNK2B |  | SOX9 | PTPN14 | CSK | RPS27A | NMNAT1 | MORF4L1 | HDAC1 |
| SPTBN1 | RNF146 |  | OTUB1 | UTRN | TIFA | Bag6 | BUD13 | COL4A3BP | HDAC3 |
| Lin7c | RPS17 |  | SMARCA5 | KPNA1 | PLEKHS1 | SIAH1 | JPH2 | CCDC33 | HDAC2 |
| RPL24 | MCM3AP |  | OTUB2 | LZTR1 | CSRP1 | SIAH2 | KIF1C | CCDC30 | CLOCK |
| TLN1 | C2CD2L |  | CEBPB | SYNM | CCDC9 | sep-08 | PIP5K1A | NCCRP1 | CIRBP |
| MBP | SPG7 |  | AXIN2 | C16orf70 | BCAR1 | HIST1H1T | DDX24 | PRKAA1 | TEX10 |
| NET1 | ERC1 |  | AXIN1 | AKNA | EPOR | KIAA0020 | BOD1L1 | BTAF1 | RCOR1 |
| PCNA | PSMD1 |  | CYTB | GORASP1 | SUPT6H | RXRA | WDR12 | MAEA | ZNF195 |
| SMARCB1 | JUND |  | FYN | SMU1 | RALY | APPL1 | CXXC1 | MAGEH1 | C1QBP |
| MCM7 | AGR3 |  | DNAJC13 | MAML1 | PPP5C | UNC13D | RPS3A | KCNJ9 | CBX8 |
| ALPP | CTNNB1 |  | CEBPZ | USP47 | TUBB | gag | NSMCE2 | ZNF408 | INF2 |
| SAMHD1 | CYP17A1 |  | PRKCI | JUP | NEIL1 | DDX27 | OGT | SBSN | MLF1 |
| CRIP1 | C17orf89 |  | CDC5L | ALDH16A1 | CLK2 | EP300 | ZBTB21 | BIRC5 | SKP2 |
| ZNF865 | CHD6 |  | SBDS | SMEK1 | CLK3 | LSM14B | KIF21B | AIP | GAS2L3 |
| PDK3 | ANKRD17 |  | NBR1 | PARP1 | SNX27 | YTHDC1 | STAU2 | ECM1 | SKP1 |
| PDK2 | CACYBP |  | WARS | RPP25L | BTK | CSNK1A1L | TOMM20 | LOR | MECOM |
| EPM2AIP1 | TAL1 |  | GNB2 | BCCIP | SNX25 | FAM195B | KCTD3 | MAP2K1 | MYH9 |
| MAPT | RPA2 |  | SLA | GINS3 | PDGFRB | KIF1A | MED4 | HIST2H2BE | TPM3 |
| SEC61A1 | SPTBN2 |  | CCNB1 | UBE2K | TPM4 | ARID5A | FAM110A | MID2 | TPM2 |
| RAE1 | SPTBN1 |  | DDX20 | LMNB1 | KRT73 | NTN1 | RPL32 | DIO2 | TPM1 |
| PARG | ANKRD11 |  | XPO6 | TP53 | TP53BP2 | DHX30 | RPS18 | PDCD2L | KIAA1671 |
| HECTD1 | RPTOR |  | FIBP | GINS4 | TCERG1 | ATP6V1E1 | ECM1 | NEFM | SIPA1 |
| SETD1A | KRT17 |  | NOTCH2 | HYOU1 | SCYL3 | ZFP62 | TTF1 | NAP1L1 | RAB13 |
| PUF60 | LPHN1 |  | NOTCH3 | ATG12 | SPRY2 | WDR12 | BAP1 | NAP1L4 | SKAP1 |
| ATP2B3 | TIMM17A |  | Dlgap2 | MELK | ATR | PIAS1 | MAP7 | NEFH | AMBRA1 |
| TROVE2 | EEF1D |  | FKBP14 | PHF7 | STXBP4 | RPL10A | NOC4L | ZNHIT6 | CEP250 |
| ITSN1 | AXIN1 |  | PMAIP1 | ADAMTS9 | FABP1 | ISY1 | CPSF3 | SUV39H1 | MRPS18B |
| ANAPC16 | MBD4 |  | CRLF3 | NDUFB11 | ITIH4 | HSP90AA1 | MYOF | PIGQ | DOCK7 |
| CIAPIN1 | TFAP2A |  | Axin1 | CD2 | KIAA1549L | XAB2 | CPSF1 | KRTAP4-12 | TRIM69 |
| ZFP1 | YWHAQ |  | UQCRQ | KRT4 | NOTCH2NL | TADA3 | RERE | FAM9B | NUDT16 |
| MYCBP2 | FYN |  | GPR39 | VDAC3 | RACGAP1 | DCP1B | DNAL4 | EPC2 | SATB2 |
| ENTPD7 | DVL2 |  | IGF2BP1 | PSTPIP1 | DNAJB1 | RPS13 | THUMPD3 | EPC1 | NAT10 |
| SCAMP3 | YWHAH |  | POLR3D | BCAS3 | MYH9 | DHX8 | TIMM17A | NDUFS1 | LRRFIP2 |
| SPAG9 | ARHGAP21 |  | POLR3E | BCR | HELZ | TMPO | FAM171B | FAM160A2 | PIP5K1A |
| HK2 | SEC31A |  | POLR3B | STAT2 | SNRPA1 | PTK2 | WASF3 | MRGBP | LY6G5B |
| TWF2 | TRIM25 |  | MAP3K2 | OBSL1 | PRPF40A | RUNDC3A | MLLT4 | HBB | BASP1 |
| FAM206A | NAT2 |  | POLR3K | USP1 | CLASRP | EDC4 | PUSL1 | PBXIP1 | AATF |
| UBR2 | YWHAB |  | POLR3H | DSG1 | PHACTR4 | BIRC7 | TSR3 | SMAP2 | CDK8 |
| UBR1 | KRT13 |  | CALM1 | MORF4L2 | H1F0 | TCEB2 | NOP56 | CCDC102A | NRF1 |
| UBR4 | HSD17B4 |  | MPP3 | RPS26 | GAPDH | SYNRG | TBX3 | CSNK2A2 | AMOTL1 |
| KCTD13 | YWHAG |  | MPP1 | BNIP3L | TXN2 | TSLP | BRIX1 | NAV2 | SVIL |
| ZNF445 | TRA2B |  | DNMT1 | USP4 | ENO1 | Parp1 | TLN1 | KLHL8 | PCBD2 |
| KCTD10 | PPP1R13B |  | DEAF1 | RABGEF1 | NKPD1 | CTNNB1 | BRPF3 | HDAC2 | MSH2 |
| KRTAP10-9 | PCNA |  | MAP3K4 | WBP11 | IGF2BP1 | CORO1C | TMEM55B | EP400NL | USP4 |
| ROBO2 | FYB |  | FAM110A | SORD | CLU | ITGB3BP | GZF1 | RNASE7 | NIFK |
| WDR59 | COPA |  | FAM110B | LGALS7 | EP300 | ACTBL2 | SIPA1L1 | VWA9 | MSH6 |
| UBC | VASN |  | NSFL1C | RPLP0P6 | POLR2J | ARID4A | CEBPZ | SERPINB8 | SPECC1 |
| SLC19A3 | DHFRL1 |  | MAGI1 | TBL1XR1 | PPP1CC | AACS | TIMM50 | RBP2 | RPRD1A |
| HIRIP3 | ANXA7 |  | ASRGL1 | RPSA | MAPK3 | SRF | RPL26L1 | SERPINB2 | GLYR1 |
| FZR1 | COPE |  | KLHDC10 | GLIDR | LIME1 | RRP8 | YWHAG | BRAT1 | MRPS15 |
| RPL7 | CARD11 |  | CUL2 | ERCC6L | C1orf27 | UGT1A7 | ZBTB2 | CSNK2A1 | MRPS14 |
| MIOS | SYBU |  | LUC7L2 | GAREML | IRS4 | SMARCA4 | TRAF3 | H2AFV | CDADC1 |
| CLTC | HGS |  | IARS | PREP | GJA9 | HHT2 | BANP | KRTAP10-9 | MRPS11 |
| KBTBD7 | UQCRFS1P1 |  | TONSL | TMPO | IRS1 | EIF2S3 | PPAN-P2RY11 | KRTAP10-1 | MRPS10 |
| GOLPH3 | CASC3 |  | CREB1 | SNTB2 | IRS2 | EIF2S2 | HOOK2 | L3MBTL3 | SORBS2 |

FIG. 5D

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| AKT1S1 | HEATR1 | | TRIM23 | DTX3 | TCP1 | KRTAP10-3 | BEST1 | ZKSCAN7 | HIP1 |
| CRMP1 | TNF | | SLC25A26 | LDHAL6B | CDK3 | CEBPA | DKC1 | UBC | IQGAP1 |
| ATG9A | PCNT | | MDM2 | EIF6 | BABAM1 | CEBPG | ORC2 | KDM5A | RICTOR |
| UBXN6 | PRKCQ | | USP33 | TXNL4A | ISY1 | MYOD1 | ORC1 | VPS72 | NSMCE4A |
| UBXN7 | TUBA4A | | GPATCH1 | PTPN21 | SH3PXD2B | CEBPE | NLE1 | ASPHD2 | DDHD1 |
| C3orf58 | CYTH2 | | Ctnnb1 | CHORDC1 | Synj1 | AQR | GTPBP4 | NFKBIB | UNC119 |
| SIRT5 | CTNNA1 | | NIN | RAB5B | SH3PXD2A | PRPF19 | LBX1 | EP400 | FYN |
| FAF1 | ACTN1 | | SNRPD2 | TLN2 | XAB2 | CPSF3 | AR | FLG | RB1 |
| ARPC2 | ECT2 | | RNF185 | TLN1 | NEU3 | MLLT6 | ATN1 | PTN | MED10 |
| POLR2A | UTP14A | | LIMA1 | ATG5 | RP11-343C2.12 | CENPH | NR2E1 | SHCBP1L | MED11 |
| HIST1H2BB | PRPF38A | | KIF5B | PCNA | PTK2 | LSM12 | LAMP2 | HAUS4 | MED12 |
| SART1 | SRSF2 | | MASP1 | PIGA | SF3B4 | NPAS2 | EPHA10 | NKAPL | MED13 |
| GET4 | TXNDC11 | | Slc25a4 | HSPB1 | SF3B1 | RPL23 | TRIP10 | CPA4 | MED14 |
| ETV1 | MYO6 | | UTRN | MCM5 | RPRD1A | ALX4 | KRTAP4-12 | DCTN5 | MED15 |
| TAF6 | PPP2R5A | | KPNA2 | MCM3 | NFYB | KLF5 | HIST2H2AB | LZTS2 | MED16 |
| TMEM65 | MBD5 | | KPNA1 | KRTAP26-1 | FGD6 | WDR36 | HIST2H2AC | UBB | MED17 |
| CDC27 | MAD1L1 | | ZBTB21 | SNRNP40 | PFDN5 | MED16 | NF1 | FAM118A | MED18 |
| CDC26 | RND2 | | DOCK8 | RHPN1 | IQGAP1 | EIF4ENIF1 | DPH1 | MTFR1 | MED19 |
| TNFAIP1 | STON2 | | Nbr1 | PPP1CA | YWHAZ | SIPA1L1 | NUDT21 | EFHC1 | CCT6A |
| RBPMS | POU3F3 | | Deaf1 | ABCC2 | DRG1 | CNOT7 | VAMP2 | GATAD1 | PACSIN3 |
| TAF9 | CREBBP | | MED24 | ILF2 | HDGFRP3 | PSMC5 | HAP1 | TRIM41 | CCT6B |
| NUP153 | C2CD5 | | GSKIP | ISL1 | INPPL1 | SIN3A | ECT2 | PRDM14 | INTS7 |
| HTT | TIA1 | | PTPN11 | PSMF1 | PACRGL | SMURF1 | RBM19 | DEPTOR | KRI1 |
| BTBD9 | PDPK1 | | RICTOR | MFHAS1 | YWHAQ | TRAF2 | LIN54 | IVL | SSNA1 |
| IPO8 | BOLA3 | | ZSCAN1 | ZFAND6 | RB1 | SMARCB1 | RPL36 | CEP170P1 | PSME3 |
| IPO9 | TPR | | SMURF2 | PUF60 | HSPD1 | ZNF7 | WDR75 | IPO8 | CAMK2D |
| BUD31 | | | USP48 | CCDC158 | YWHAH | PDIA6 | MEAF6 | IPO9 | AP2A1 |
| IPO7 | | | SENP8 | TPX2 | HCLS1 | PSME4 | MELK | IPO7 | CASC5 |
| IPO5 | | | JUN | AHCYL1 | XRCC6 | NR4A1 | NOC3L | KDM1A | TUBA4A |
| RNF123 | | | PPARGC1A | WWC2 | CCT6A | PSME2 | RPL30 | POF1B | GNB2 |
| ACTR2 | | | NARS | WWC1 | YWHAG | sep-04 | CSTF2 | USP15 | CALD1 |
| MAPK14 | | | PIAS1 | LYZ | YWHAE | RTN2 | TARBP2 | ME1 | MTFR1L |
| MAPK11 | | | RBM39 | DSC1 | NDUFS6 | MCM6 | KIF13B | GADL1 | DDX27 |
| NPLOC4 | | | MAP1B | GOLGA2 | ANXA6 | AR | SPTY2D1 | LMNA | EDRF1 |
| NCOR1 | | | GBP2 | KHK | EEF1A1P5 | MCM3 | ZNF92 | TNPO2 | NRIP1 |
| TNPO1 | | | UBA1 | CREBRF | PSME3 | SKIL | HCFC1 | CYTH2 | LIMCH1 |
| NR6A1 | | | SPICE1 | IL36RN | PSME1 | TMX3 | KAT6A | CCDC105 | ACTG1 |
| TBC1D4 | | | TP53 | PRRC2B | CASC3 | ALOX15B | MUT | HNRNPU | DYNLL2 |
| TECR | | | MELK | P4HB | HIST1H3A | BRMS1L | WDR74 | HIST2H2AC | FCHO2 |
| HSPA12B | | | EIF4EBP1 | SPAG5 | AP2A1 | RBM14-RBM4 | svp | HNRNPK | MYL6 |
| HSPA12A | | | LRCH2 | ATP2B1 | AP2A2 | CTNNA1 | WDR76 | HNRNPM | CCT4 |
| NFKB1 | | | PPP2R5D | EIF4G3 | TUBA4B | RPL28 | | MAPK9 | MYL9 |
| CECR6 | | | UBE2S | EIF4G2 | ABI3 | EIF4E3 | | ASH1L | SUGT1 |
| ZGLP1 | | | UBE2W | EIF4G1 | CUL4A | SNW1 | | PDSS1 | CALM1 |
| ATP12A | | | NADK | FZR1 | MAP4K1 | RPL26L1 | | SYNE2 | DNMT1 |
| RAI1 | | | SMN2 | KRTAP10-3 | NKTR | CASP3 | | PHLPP1 | RORC |
| AMFR | | | BAG6 | ADAM8 | ARHGAP35 | RPL38 | | TNFRSF13B | RORB |
| HIST1H1A | | | ADIRF | KRTAP10-7 | TWISTNB | ABI2 | | TNFRSF13C | THRA |
| Dlg1 | | | RPS2 | GRB2 | WIPF3 | SRRM2 | | ZNF521 | DLGAP1 |
| YTHDC1 | | | CTNND1 | XRN1 | WIPF2 | NRIP1 | | ZNF529 | NEXN |
| Dlg3 | | | ARRB1 | UBC | WIPF1 | EZR | | ZNF131 | CLINT1 |
| BSG | | | RPL36AL | KRTAP10-5 | ACTG1 | TBC1D10B | | NUMA1 | WDR62 |
| Dlg4 | | | BCAS2 | RPL8 | NISCH | PSAT1 | | TEX35 | WDR60 |
| EMP2 | | | RBM8A | RFXANK | KRT32 | NONO | | CLPB | LSS |
| PIAS4 | | | DHX58 | EP400 | KRT35 | Grip1 | | FBXO39 | ZNF207 |
| PSMB6 | | | ZHX1 | DNM2 | KRT34 | TIMM13 | | CAND2 | BRCA2 |
| FBL | | | CBY1 | FLG | KRT36 | ACTL6A | | PDZD11 | TRIM29 |
| NUMA1 | | | MARK4 | PLXNB1 | C7orf55 | G3BP2 | | CTU2 | ACOT7 |
| HAX1 | | | MARK1 | FATE1 | RAPGEF1 | ATF5 | | RFTN1 | MTPAP |
| DCAF13 | | | MARK2 | TERF1 | SNRNP200 | ATF4 | | UBE2G1 | SHMT2 |
| DDOST | | | MARK3 | CRMP1 | CALM3 | CMTM5 | | SIN3B | USP36 |
| CAND1 | | | HIST2H2AA3 | LZTS2 | MAP3K1 | CALCOCO2 | | SIN3A | FGFR1 |
| PLOD2 | | | MSH2 | KLHL36 | BCLAF1 | ATF3 | | HOOK2 | DZIP3 |
| SLC9A3R2 | | | SRC | KIAA0368 | PARD6A | POU2F1 | | HOOK3 | MORN3 |
| SIN3B | | | EPB41L3 | IFT74 | DLGAP1 | | | HOOK1 | LIMA1 |
| NR3C1 | | | USP4 | SGTA | ERBB2 | | | DMKN | MYLK |
| MADD | | | NDUFA9 | TRIM46 | SHC1 | | | ARMC8 | RAI14 |
| Cask | | | TPD52L2 | MTFR1 | PNKP | | | NDEL1 | KIF22 |
| MAP7D1 | | | IGSF21 | SART1 | TRIM27 | | | NF1 | NKAP |

FIG. 5E

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| USP11 | | | UCHL5 | ETV6 | SLC25A6 | | | BRAP | NUCKS1 |
| HSPA14 | | | LGALS1 | CEP170P1 | SLC25A5 | | | CCDC120 | MYO5C |
| TXNDC11 | | | QARS | LRRC15 | CHERP | | | TMEM39A | MYO5B |
| ATF1 | | | UCHL1 | BTBD9 | GPATCH8 | | | ACTL6A | MYO5A |
| ATF2 | | | UCHL3 | BTBD8 | DNAJA3 | | | TUBA1A | CD109 |
| | | | SGK3 | ANKEF1 | PTPN18 | | | | MED29 |
| | | | FARSB | KDM1A | INPP5D | | | | MED28 |
| | | | FIS1 | HNRNPH1 | GAREM | | | | PNRC1 |
| | | | C14orf1 | NCOR1 | SYK | | | | MED21 |
| | | | PDE4D | SNRPF | PTPN12 | | | | MED20 |
| | | | PPIB | CNKSR1 | PTPN11 | | | | MED23 |
| | | | DTX3 | GCN1L1 | INCA1 | | | | MED22 |
| | | | BIRC3 | SNRPG | RBBP6 | | | | MED24 |
| | | | BIRC2 | PDCD4 | KIT | | | | MED27 |
| | | | CYCS | MAPK9 | TTC14 | | | | MED26 |
| | | | FOXO1 | POMP | NKAP | | | | NOP14 |
| | | | MAP4 | RCC1 | KPNA2 | | | | NOP16 |
| | | | SPTBN4 | DTNB | SYNM | | | | XRCC1 |
| | | | Krba1 | PHLPP2 | FAM98B | | | | SEC16A |
| | | | CLEC3B | PHLPP1 | SKAP2 | | | | sep-07 |
| | | | DPP8 | SYNE4 | DOCK1 | | | | FAM13A |
| | | | DPP9 | VPS26A | GAB2 | | | | ZSCAN1 |
| | | | LPCAT1 | VPS36 | GAB3 | | | | sep-02 |
| | | | EYA1 | PKD1 | DOCK4 | | | | SRSF5 |
| | | | MID1IP1 | ID2 | GAB1 | | | | STIL |
| | | | RBCK1 | GLB1 | ARHGAP9 | | | | AHNAK |
| | | | ILKAP | NXT2 | XRCC1 | | | | SRSF9 |
| | | | PPP6R3 | CSE1L | CRK | | | | TCP1 |
| | | | Gm4779 | MKI67 | XRCC5 | | | | MKS1 |
| | | | PPP1CA | ZNF250 | LY86 | | | | JUP |
| | | | AQR | CHGB | AP2S1 | | | | NPPA |
| | | | CYC1 | STRA13 | SRSF6 | | | | COBL |
| | | | PRPF19 | ACAD11 | SRSF1 | | | | UBA1 |
| | | | Dvl1 | COTL1 | STAT5B | | | | CORO2A |
| | | | MAPT | UBQLN4 | AGTRAP | | | | GPHN |
| | | | ISY1-RAB43 | TTLL12 | AHNAK | | | | UBE2I |
| | | | UFD1L | SIN3B | SRSF9 | | | | RBFOX2 |
| | | | BCL3 | LDHA | VPS37B | | | | MRPS28 |
| | | | CKAP5 | SIN3A | PCDHB5 | | | | GNAS |
| | | | DARS | SLC39A10 | DNAJB11 | | | | MED13L |
| | | | SRP9 | PABPN1 | RBM33 | | | | MRPS24 |
| | | | AKT2 | TRAF6 | MAP1A | | | | PRTFDC1 |
| | | | RBPJ | TRAF7 | PRKAB1 | | | | CDC14B |
| | | | MICAL1 | USP15 | HOMEZ | | | | MRPS21 |
| | | | FAM193B | SNRPB | PARP1 | | | | CAMKK2 |
| | | | MYC | SSBP3 | UBA1 | | | | POLE2 |
| | | | AURKA | NPM1 | PTPN1 | | | | PHF8 |
| | | | ENTPD6 | NAGK | PTPN6 | | | | PHF2 |
| | | | DDIT4 | SEC22B | TNFRSF1A | | | | RASIP1 |
| | | | SOD1 | DIS3 | WARS | | | | MYO1E |
| | | | KCTD11 | UNC45A | RPAP2 | | | | DSN1 |
| | | | SMAD1 | ZBTB43 | ARHGEF7 | | | | MYO1B |
| | | | GIPC1 | | TOP3A | | | | RPS2 |
| | | | UBR1 | | SYN1 | | | | FBXO7 |
| | | | UBR5 | | NADK | | | | RPL36AL |
| | | | CRCP | | BAG1 | | | | RAF1 |
| | | | MLLT4 | | CTDP1 | | | | BTBD10 |
| | | | PCGF6 | | LAX1 | | | | NUSAP1 |
| | | | EEF1G | | KRT2 | | | | CEP162 |
| | | | GSK3B | | KRT1 | | | | BMP2K |
| | | | INADL | | KRT7 | | | | TCEB3 |
| | | | UBC | | KRT5 | | | | RABEP1 |
| | | | RPL9 | | KRT4 | | | | DSG2 |
| | | | DCLK1 | | CYP2S1 | | | | NMNAT1 |
| | | | FEN1 | | PSTPIP2 | | | | KDR |
| | | | SLC25A38 | | KRT9 | | | | GOLGA5 |
| | | | PTN | | KRT8 | | | | SRC |
| | | | CHD3 | | A2M | | | | RABGEF1 |
| | | | NMD3 | | BCR | | | | CCDC36 |

FIG. 5F

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| | | | BEX1 | | JMJD4 | | | | SORD |
| | | | TUBA1A | | MICAL1 | | | | ZC3HAV1L |
| | | | NOTCH1 | | KRT81 | | | | PAWR |
| | | | FATE1 | | KRT82 | | | | CCDC132 |
| | | | PLEKHA7 | | KRT83 | | | | MYL12A |
| | | | UBXN6 | | KRT85 | | | | MRPS16 |
| | | | EPM2A | | KRT86 | | | | ARPC5L |
| | | | NCOA3 | | SNX18 | | | | EIF2AK4 |
| | | | PGM1 | | KRT6A | | | | MRPS26 |
| | | | GYS1 | | ND4 | | | | PALLD |
| | | | POLR2A | | SRC | | | | STX12 |
| | | | MIA3 | | CD59 | | | | MYO19 |
| | | | TMEM44 | | RPS20 | | | | WDR19 |
| | | | POLR2H | | PHC2 | | | | PPIA |
| | | | ANKRD28 | | WBP11 | | | | EFHD2 |
| | | | STAT1 | | SRM | | | | MRPS25 |
| | | | USP51 | | CD180 | | | | ANTXR1 |
| | | | SNCA | | WAS | | | | PPP1R1C |
| | | | FUCA1 | | ZMAT1 | | | | MRPS23 |
| | | | NRBP1 | | MYL12B | | | | CORO1B |
| | | | KDM1A | | MYL12A | | | | CORO1C |
| | | | STAMBP | | GAREML | | | | MAP6 |
| | | | SDCBP | | E2F2 | | | | NOC4L |
| | | | Spice1 | | MAGOH | | | | SPTBN2 |
| | | | CWF19L2 | | WDR12 | | | | YES1 |
| | | | ZNF746 | | RPRD1B | | | | RNF170 |
| | | | NANOG | | PPIG | | | | NAP1L1 |
| | | | FZD5 | | PPIE | | | | RPL26 |
| | | | TBK1 | | BLNK | | | | RPL22 |
| | | | LGALS14 | | PDE4D | | | | MRPS7 |
| | | | AP2M1 | | ASAP1 | | | | MRPS6 |
| | | | MAPK1 | | ASAP2 | | | | TPRG1 |
| | | | HNRNPM | | OCRL | | | | ATP5G1 |
| | | | NFKB1 | | MAP4K3 | | | | STRN |
| | | | SNRNP70 | | MAP4K5 | | | | ANXA2 |
| | | | PRUNE | | CUTA | | | | LRCH2 |
| | | | NUB1 | | BPGM | | | | MRPL19 |
| | | | SYDE1 | | CYFIP2 | | | | GLTSCR2 |
| | | | TPD52 | | KIRREL | | | | PPP1CB |
| | | | SYNE1 | | MAP2 | | | | PPP1CC |
| | | | PHLPP1 | | AEBP1 | | | | PPP1CA |
| | | | SYNE4 | | PSMD13 | | | | NOC3L |
| | | | CRNKL1 | | SPTBN1 | | | | PICALM |
| | | | ZCRB1 | | PTPN23 | | | | ZNF512B |
| | | | MTF2 | | HIST4H4 | | | | NGDN |
| | | | SREBF1 | | MLLT4 | | | | TMOD1 |
| | | | PRKACA | | KRT33B | | | | TMOD3 |
| | | | RNF144A | | AMBP | | | | LZTFL1 |
| | | | HSP90AA1 | | NAP1L5 | | | | GSN |
| | | | ZNF135 | | FAU | | | | CCDC102A |
| | | | KCTD2 | | NUTM2F | | | | CCDC88A |
| | | | KCTD6 | | SYNJ1 | | | | ANAPC16 |
| | | | ARL3 | | HNRNPA2B1 | | | | DDX31 |
| | | | ARL2 | | SYNJ2 | | | | WHSC1L1 |
| | | | PFKFB4 | | EYA3 | | | | CYBRD1 |
| | | | RIPK1 | | ANXA2 | | | | HSP90AB1 |
| | | | Map3k11 | | PEAK1 | | | | ARHGAP21 |
| | | | CACYBP | | MSI2 | | | | MICAL3 |
| | | | U2AF2 | | KRT10 | | | | FLII |
| | | | FAM83D | | IK | | | | CSNK2A1 |
| | | | CREB3L3 | | Dnm1 | | | | NEK9 |
| | | | TSR1 | | NIF3L1 | | | | NARFL |
| | | | GLI2 | | DYNC1H1 | | | | LYN |
| | | | GLI1 | | FLNA | | | | ZAP70 |
| | | | PIM2 | | MCM8 | | | | AURKB |
| | | | CLASP2 | | FAM154B | | | | NUF2 |
| | | | TRAF6 | | CASP2 | | | | HK2 |
| | | | PDIA5 | | ARAP1 | | | | MYO1C |
| | | | PDIA3 | | PPP1CA | | | | ZNF362 |

FIG. 5G

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| | | | DNMT3L | | FAM9B | | | | MRPS2 |
| | | | AR | | SRRM2 | | | | TSPAN2 |
| | | | USP14 | | RPA1 | | | | CEBPZ |
| | | | USP15 | | DRD3 | | | | C12orf40 |
| | | | ALDH1B1 | | PON2 | | | | ATG2B |
| | | | ABCC10 | | EIF4A3 | | | | UBR5 |
| | | | TXNDC17 | | TOM1L1 | | | | TWF1 |
| | | | AARS | | FASLG | | | | TWF2 |
| | | | RPL30 | | WDR83OS | | | | BARHL1 |
| | | | UPF3B | | HCVgp1 | | | | PPP2CA |
| | | | GRIN2A | | MDFI | | | | ARPC1B |
| | | | ATF3 | | LAT2 | | | | FZR1 |
| | | | ACTL6B | | DARS | | | | ELFN2 |
| | | | DNM1L | | PBXIP1 | | | | CCDC86 |
| | | | BAP1 | | NKX2-5 | | | | L3MBTL3 |
| | | | Vta1 | | NTRK1 | | | | GRB2 |
| | | | Prox2 | | HSP90AB1 | | | | ZKSCAN4 |
| | | | | | SMAD4 | | | | CCNC |
| | | | | | TTYH2 | | | | CCDC93 |
| | | | | | LIG3 | | | | SPC25 |
| | | | | | MYC | | | | UQCC2 |
| | | | | | Mta1 | | | | MACF1 |
| | | | | | Mta3 | | | | PHF21A |
| | | | | | CD28 | | | | H2AFY |
| | | | | | SOD1 | | | | SPECC1L |
| | | | | | CD22 | | | | DEK |
| | | | | | ALOX5 | | | | CLTA |
| | | | | | RANGAP1 | | | | CLTC |
| | | | | | DPPA4 | | | | CLTB |
| | | | | | TSPAN2 | | | | CCHCR1 |
| | | | | | YWHAB | | | | PNMA3 |
| | | | | | RBP4 | | | | THAP11 |
| | | | | | PRAP1 | | | | JMY |
| | | | | | HSPG2 | | | | HAUS6 |
| | | | | | UBR4 | | | | HAUS7 |
| | | | | | SOCS4 | | | | HAUS5 |
| | | | | | SOCS1 | | | | HAUS3 |
| | | | | | EEF1G | | | | MED12L |
| | | | | | EEF1D | | | | TRO |
| | | | | | MST1R | | | | SAMD1 |
| | | | | | CD2AP | | | | PIK3R1 |
| | | | | | GRB2 | | | | PCBP1 |
| | | | | | HUNK | | | | LZTS2 |
| | | | | | UBC | | | | ZFC3H1 |
| | | | | | GPALPP1 | | | | TROAP |
| | | | | | CCT6B | | | | MRPL13 |
| | | | | | UQCC2 | | | | SDAD1 |
| | | | | | HP | | | | RAB3GAP1 |
| | | | | | RPL5 | | | | ARPC3 |
| | | | | | FMN1 | | | | ARPC2 |
| | | | | | NR3C1 | | | | MED30 |
| | | | | | FH | | | | MED31 |
| | | | | | DNM1 | | | | ARPC4 |
| | | | | | PPP1R21 | | | | DSTN |
| | | | | | CLTC | | | | PLEC |
| | | | | | DNM2 | | | | ITPR2 |
| | | | | | PNMA5 | | | | ITPR3 |
| | | | | | NCKAP1 | | | | KIAA1109 |
| | | | | | TP53RK | | | | MISP |
| | | | | | LRRK1 | | | | PEX5 |
| | | | | | AP4S1 | | | | TLK2 |
| | | | | | FAM175B | | | | VAV1 |
| | | | | | CMAS | | | | TNFAIP1 |
| | | | | | PIK3R3 | | | | RBPMS |
| | | | | | PIK3R2 | | | | STON2 |
| | | | | | PIK3R1 | | | | SPC24 |
| | | | | | LZTS2 | | | | ACTR3 |
| | | | | | SH2D4A | | | | ACTR2 |
| | | | | | SH2D5 | | | | CFL2 |

FIG. 5H

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| | | | | | LNX1 | | | | KDM1A |
| | | | | | LMX1A | | | | ACE |
| | | | | | ARPC4 | | | | STOM |
| | | | | | POLR2E | | | | DIABLO |
| | | | | | POLR2D | | | | ABL1 |
| | | | | | POLR2G | | | | GNAI2 |
| | | | | | POLR2F | | | | NCOR1 |
| | | | | | PLEC | | | | GNAI1 |
| | | | | | DAG1 | | | | SCML1 |
| | | | | | POLR2C | | | | PIK3C2A |
| | | | | | POLR2B | | | | MRPS34 |
| | | | | | POLR2M | | | | MRPS33 |
| | | | | | POLR2L | | | | AP2M1 |
| | | | | | POLR2I | | | | PPP1R12A |
| | | | | | KIF3A | | | | PPP1R12B |
| | | | | | VCP | | | | SRD5A1 |
| | | | | | VAV3 | | | | SNRNP70 |
| | | | | | VAV2 | | | | TUFT1 |
| | | | | | USP53 | | | | HELLS |
| | | | | | SHBG | | | | SEL1L |
| | | | | | HTT | | | | HMGA1 |
| | | | | | RBM22 | | | | BCOR |
| | | | | | ELMO2 | | | | BCAP31 |
| | | | | | BUD31 | | | | YTHDC1 |
| | | | | | GRPEL1 | | | | ACTRT1 |
| | | | | | GPANK1 | | | | ARHGAP11A |
| | | | | | WBSCR27 | | | | WIZ |
| | | | | | STAMBP | | | | AMOT |
| | | | | | EPHA2 | | | | RPS12 |
| | | | | | PIK3AP1 | | | | UTP3 |
| | | | | | LY6G6F | | | | ZNF318 |
| | | | | | ABL1 | | | | DNM2 |
| | | | | | NPLOC4 | | | | RHOXF2 |
| | | | | | SHKBP1 | | | | LCA5 |
| | | | | | IKZF3 | | | | MSN |
| | | | | | TEC | | | | FAM83H |
| | | | | | HNRNPU | | | | ANKHD1 |
| | | | | | REPS2 | | | | CACTIN |
| | | | | | AP2M1 | | | | RAB36 |
| | | | | | HNRNPK | | | | RAB34 |
| | | | | | GPN3 | | | | BCL2L11 |
| | | | | | PPP1R12A | | | | C14orf80 |
| | | | | | GPN1 | | | | TSR1 |
| | | | | | HNRNPC | | | | CPNE1 |
| | | | | | HNRNPD | | | | RPS19BP1 |
| | | | | | REEP6 | | | | AHDC1 |
| | | | | | CECR2 | | | | KCTD20 |
| | | | | | NKD2 | | | | DAPK3 |
| | | | | | POMP | | | | TSSC1 |
| | | | | | ARL6IP4 | | | | PLS1 |
| | | | | | ABI3BP | | | | ESF1 |
| | | | | | TCEAL8 | | | | TFAM |
| | | | | | CRNKL1 | | | | HOOK1 |
| | | | | | FHOD1 | | | | ACAP1 |
| | | | | | FAAH | | | | LUZP1 |
| | | | | | SOS2 | | | | CFL1 |
| | | | | | SOS1 | | | | PLEKHG3 |
| | | | | | SLAIN2 | | | | ACTN1 |
| | | | | | SMU1 | | | | ACTN4 |
| | | | | | MET | | | | RPL36 |
| | | | | | APLN | | | | PRPF38A |
| | | | | | HSP90AA1 | | | | RNF169 |
| | | | | | BRE | | | | UNC45A |
| | | | | | CLPX | | | | IMMT |
| | | | | | DNM3 | | | | NEDD4L |
| | | | | | PPCDC | | | | PTRF |
| | | | | | RPS19 | | | | |
| | | | | | TOMM22 | | | | |
| | | | | | PDCD6IP | | | | |

FIG. 51

| miR-150-5p | miR-215-5p | miR-192-5p | miR-92b-3p | miR-486-3p | miR-16-5p | miR-148a-3p | miR-22-3p | miR-30b-5p | miR-30c-5p |
|---|---|---|---|---|---|---|---|---|---|
| | | | | | HSPA1B | | | | |
| | | | | | PDCL | | | | |
| | | | | | HSPA1L | | | | |
| | | | | | TXN | | | | |
| | | | | | UBASH3B | | | | |
| | | | | | THRAP3 | | | | |
| | | | | | AQR | | | | |
| | | | | | PRPF19 | | | | |
| | | | | | TRAT1 | | | | |
| | | | | | ARHGAP32 | | | | |
| | | | | | DOK3 | | | | |
| | | | | | DOK1 | | | | |
| | | | | | PXN | | | | |
| | | | | | TTLL12 | | | | |
| | | | | | TF | | | | |
| | | | | | USP6NL | | | | |
| | | | | | SH3KBP1 | | | | |
| | | | | | SNTA1 | | | | |
| | | | | | RABGEF1 | | | | |
| | | | | | CLASP2 | | | | |
| | | | | | MLXIPL | | | | |
| | | | | | ORC2 | | | | |
| | | | | | ACAP1 | | | | |
| | | | | | ESD | | | | |
| | | | | | FBF1 | | | | |
| | | | | | SHANK3 | | | | |
| | | | | | RASA1 | | | | |
| | | | | | TAB1 | | | | |
| | | | | | CD164 | | | | |
| | | | | | TUBA1C | | | | |
| | | | | | PTPRE | | | | |
| | | | | | C1orf94 | | | | |
| | | | | | ACTL6A | | | | |
| | | | | | PTPRA | | | | |
| | | | | | MYOZ1 | | | | |
| | | | | | PTPRJ | | | | |
| | | | | | GSTK1 | | | | |

FIG. 5J hsa-miR-30b-5p hsa-miR-150-5p hsa-miR-150-5P hsa-miR-4732-3p

PREDICTING CARDIOTOXICITY RISK IN CANCER PATIENTS RECEIVING ANTHRACYCLINES CHEMOTHERAPY

FIELD OF THE INVENTION

The present invention relates generally to the field of Oncology and Toxicology. Particularly, the invention relates to a method for predicting cardiotoxicity risk in cancer patients receiving, or susceptible to receive, anthracyclines chemotherapy. The method is based on the analysis of the expression levels of a set of 10 circulating miRNAs.

BACKGROUND OF THE INVENTION

Anthracyclines are well-established and effective antineoplastic drugs currently used alone or in combination with other anti-mitotic agents for the treatment of a wide variety of tumors including breast cancer (Palmieri C, Krell J, James C R, et al. *Rechallenging with anthracyclines and taxanes in metastatic breast cancer. Nat Rev Clin Oncol* 2010; 7 (10): 561-741). However, its implementation is related with several collateral effects, being cardiotoxicity the most severe. Usually, the first symptoms appear within the first year of administration of the last dose, but it may occur even after 6-10 years after administration (Cardinale D, Colombo A, Bacchiani G, et al. *Early detection of anthracycline cardiotoxicity and improvement with heart failure therapy. Circulation* 2015; 131 (22): 1981-82).

Anthracyclines induced cardiotoxicity (AC) is considered acute if occurs shortly after its administration (Cardinale D. et al; *Takemura G, Fujiwara H. Doxorubicin-induced cardiomyopathy from the cardiotoxic mechanisms to management. Prog Cardiovasc Dis* 2007; 49 (5): 330-52). However, since the toxicity of anthracyclines is cumulative, the most common type of AC occurs several years after the treatment what is known as chronic cardiotoxicity. Since the heart is a post-mitotic organ, once the myocardium is damaged the deterioration of heart function is commonly progressive. Early assessment for cardiac toxicity following anthracycline treatment could aid to perform a more precise risk stratification of patients who may benefit from more frequent surveillance cardiac function.

miRNAs have been involved in pivot biological processes such as drug resistance (Ahmad N, Haider S, Jagannathan S, Anaissie E, Driscoll J J. *MicroRNA theragnostics for the clinical management of multiple myeloma. Leukemia* 2014; 28 (4): 732-8), cellular damage or cancer (Allegra A, Alonci A, Campo S, et al. *Circulating microRNAs: new biomarkers in diagnosis, prognosis and treatment of cancer (review). Int J Oncol* 2012; 41 (6): 1897-912). These molecules are a small class of single trans noncoding RNAs between 20-25 nucleotides that control expression of mRNAs at the post-transcriptional level by targeting the 3'untranslated region of mRNA transcripts (*Ambros V. The functions of animal microRNAs. Nature* 2004; 431 (7006): 350-5). They can cleave complementary messenger mRNA targets and diminish the translation of partially complementary targets (Kim V N. *MicroRNA biogenesis: coordinated cropping and dicing. Nat Rev Mol Cell Biol* 2005; 6 (5): 376-85). These short molecules have high specificity and many of them have a tissue specific expression (Latronico M V, Catalucci D, Condorelli G. *Emerging role of microRNAs in cardiovascular biology. Circ Res* 2007; 101 (12): 1225-36). Due to its high stability in plasma and serum and easy detection they have been used as biomarkers in different pathologies including cancer (Hamam R, Hamam D, Alsaleh K A, et al. *Circulating microRNAs in breast cancer: novel diagnostic and prognostic biomarkers. Cell Death Dis* 2017; 8 (9): e3045) and cardiac diseases (Gilad S, Meiri E, Yogev Y, et al. *Serum microRNAs are promising novel biomarkers. PLOS One* 2008; 3 (9): e3148; Mitchell P S, Parkin R K, Kroh E M, et al. *Circulating microRNAs as stable blood-based markers for cancer detection. Proc Natl Acad Sci USA* 2008; 105 (30): 10513-8; Schulte C, Zeller T. *microRNA-based diagnostics and therapy in cardiovascular disease-Summing up the facts. Cardiovasc Diagn Ther* 2015; 5 (1): 17-36) and specific patterns of circulating miRNAs have been associated with heart failure (Tijsen A J, Creemers E E, Moerland P D, et al. *MiR423-5p as a circulating biomarker for heart failure. Circ Res* 2010; 106 (6): 1035-9) and myocardial infarction (Wang G K, Zhu J Q, Zhang J T, et al. *Circulating microRNA: a novel potential biomarker for early diagnosis of acute myocardial infarction in humans. Eur Heart J* 2010; 31 (6): 659-66). This circulating miRNAs were found stable under unfavourable conditions as high or low PH, boiling and multiple freeze-thaw cycles (Mitchell P S, Parkin R K, Kroh E M, et al. *Circulating microRNAs as stable blood-based markers for cancer detection. Proc Natl Acad Sci USA* 2008; 105 (30): 10513-8; Lawrie C H, Gal S, Dunlop H M, et al. *Detection of elevated levels of tumour-associated microRNAs in serum of patients with diffuse large B-cell lymphoma. Br J Haematol* 2008; 141 (5): 672-5) suggesting that circulating miRNAs are protected from degradation.

Currently there are few studies linking treatment with anthracyclines and the detection of circulating microRNAs. Using induced pluripotent stem cells (iPSC) derived cardiomyocytes (CM) treated with Doxorubicin it was shown a deregulation of miR-187-3p, miR-182-5p, miR-486-3p, miR-486-5p, miR-34a-3p, miR-4423-3p, miR-34c-3p, miR-34c-5p and miR-1303 in treated cells in comparison to non-treated controls (Chaudhari U, Nemade H, Gaspar J A, Hescheler J, Hengstler J G, Sachinidis A. *MicroRNAs as early toxicity signatures of doxorubicin in human-induced pluripotent stem cell-derived cardiomyocytes. Arch Toxicol* 2016; 90 (12): 3087-98). In vivo, it was reported the usefulness of miR-208 (Calvano J, Achanzar W, Murphy B, et al. *Evaluation of microRNAs-208 and 133a/b as differential biomarkers of acute cardiac and skeletal muscle toxicity in rats. Toxicol Appl Pharmacol* 2015; Nishimura Y, Kondo C, Morikawa Y, et al. *Plasma miR-208 as a useful biomarker for drug-induced cardiotoxicity in rats. J Appl Toxicol* 2015; 35 (2): 173-80), miR-133a/b, miR146a (Horie T, Ono K, Nishi H, et al. *Acute doxorubicin cardiotoxicity is associated with miR-146a-induced inhibition of the neuregulin-ErbB pathway. Cardiovasc Res* 2010; 87 (4): 656-64) and miR-34a (Desai V G, J CK, Vijay V, et al. *Early biomarkers of doxorubicin-induced heart injury in a mouse model. Toxicol Appl Pharmacol* 2014; 281 (2): 221-9) as useful biomarkers for drug-induced cardiotoxicity in rats. Recently, the levels of several miRNAs were analyzed in blood of childhood patients treated with anthracyclines and determined that only miR-29b and miR-499 significantly correlated with cumulative anthracycline dosage shortly after infusion (Leger K J, Leonard D, Nielson D, de Lemos J A, Mammen P P, Winick N J. *Circulating microRNAs: Potential Markers of Cardiotoxicity in Children and Young Adults Treated With Anthracycline Chemotherapy. J Am Heart Assoc* 2017; 6 (4)). In this context, some molecular prognostic classifiers based on miRNA detection have been developed for cardiac induced toxicity after treatment with Trastuzumab (Ezaz G, Long J B, Gross C P, Chen J. *Risk prediction model for heart failure and cardiomyopathy after* adjuvant trastuzumab therapy for breast cancer. *J Am Heart Assoc* 2014; 3 (1): e000472) or anthracyclines (Leger K J, Leonard D, Nielson D, de Lemos J A, Mammen P P, Winick N J. *Circulating microRNAs: Potential Markers of Cardiotoxicity in Children and Young Adults Treated With Anthracycline Chemotherapy. J Am Heart Assoc* 2017; 6 (4); Leger K, Slone T, Lemler M, et al. *Subclinical cardiotoxicity in childhood cancer survivors exposed to very low dose anthracycline therapy. Pediatr Blood Cancer* 2015; 62 (1): 123-7; Lipshultz S E, Diamond M B, Franco V I, et al. *Managing chemotherapy-related cardiotoxicity in survivors of childhood cancers. Paediatr Drugs* 2014; 16 (5): 373-89). However, none of them can be used for personalized risk assessment before the initiation of chemotherapy.

The present invention provides a novel predictive model based on the combination of ten selected circulating miRNAs that can be used to stratify cancer patients at risk of cardiotoxicity.

The definition of this microRNA signature for cardiotoxic risk in cancer patients can be used for decision making of treatment regimens together with the monitorization of cardiotoxicity in cancer patients treated with anthracyclines.

BRIEF DESCRIPTION OF THE DRAWINGS

FIG. 5 (I-J). Target genes of the 10 miRNAs (miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p).

DETAILED DESCRIPTION OF THE INVENTION

Figure 1:
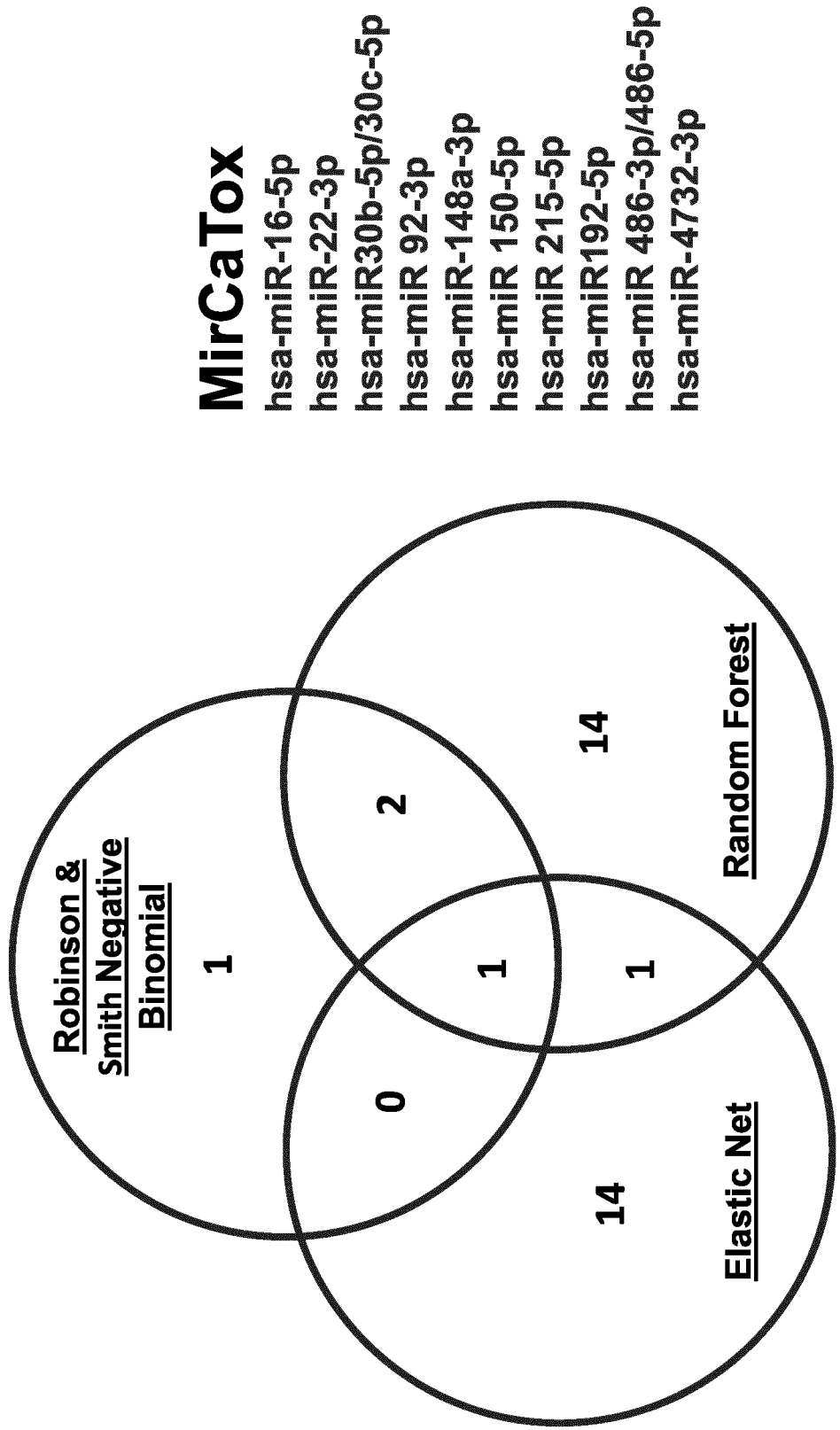
FIG. 1. Venn diagram of the overlap of miRNA profiles differentially expressed between cases and controls in miRNAseq array and list of the 10 miRNAs.

The present invention provides with new biomarkers of prediction of cardiotoxicity risk in cancer patients receiving, or susceptible to receive, anthracyclines chemotherapy.

In particular, the authors have developed a microRNA signature consisting of 10 circulating miRNAs: miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p, that allows the identification of patients with high risk to suffer a decline of cardiac function after anthracyclines treatment.

The alteration of the expression of these miRNAs, comparing with the expression of said miRNAs in a control subject, not suffering from cardiotoxicity, is indicative of cardiotoxicity risk.

In the present invention, a control subject is a cancer patient not suffering from cardiotoxicity after anthracycline treatment.

For the purposes of the present invention, cardiotoxicity is defined, according to the most recent clinical guidelines, as the presence, in transthoracic echocardiography performed by a qualified physician, of one of the following situations:

1. A reduction of Left Ventricle Ejection Fraction (LVEF) >5% to a final LVEF <55%, with symptoms of heart failure, or
2. A reduction of LVEF >10% to a final LVEF <55, without the presence of symptoms.

According to the above, in a main aspect, the present invention refers to the use of a set of 10 circulating miRNAs, consisting of miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p, as biomarker of prediction of cardiotoxicity risk in cancer patients receiving, or susceptible to receive, anthracyclines chemotherapy.

This new miRNA signature has allowed the authors of the invention to develop a method for predicting cardiotoxicity risk in a cancer patient receiving, or susceptible to receive, anthracyclines chemotherapy. This method comprises the following steps:

i. Determining the expression levels of a combination of 10 circulating miRNAs consisting of miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p, in a biological sample isolated from the patient, and ii. Comparing the expression levels determined in i) with the expression levels of said miRNAs from a biological sample isolated from a control subject, wherein the alteration of the expression of these miRNAs, comparing with the expression of said miRNAs in a control subject not suffering from cardiotoxicity, is indicative of cardiotoxicity risk.

In addition, based on this miRNA signature, the authors of the present invention have developed methods that, linked to an algorithm, allow cardiotoxicity to be detected with a probabilistic value, which is very useful in making clinical decisions. These methods can be used to screen cardiotoxic risk in patient's cohort receiving anthracyclines treatment or that are going to be subjected to anthracyclines chemotherapy and be used as powerful tools for cardiotoxic risk stratification of cancer patients.

Preferably, the probability of suffering from cardiotoxicity in a cancer patient receiving, or susceptible to receive, anthracyclines chemotherapy is calculated according to the following formula:

$$Pr(\text{Cardiotoxicity}) = \frac{e^{LP}}{1 + e^{LP}}$$

wherein,
LP=−1.228−0.041*miR4732−0.066*miR22−0.02*miR30b+0.081*miR16−0.053*miR148a+0.012*miR192−0.009*miR150p−0.055*miR215+0.0899*miR486

Therefore, in another aspect, the present invention refers to an in vitro method for predicting the cardiotoxicity risk probability in a cancer patient receiving, or susceptible to receive, anthracyclines chemotherapy comprising:

a) Determining the expression levels of a combination of 10 circulating miRNAs consisting of miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p, in a biological sample isolated from the patient, and b) Introducing the expression data obtained in a) in the following equation:

$$Pr(\text{Cardiotoxicity}) = \frac{e^{LP}}{1 + e^{LP}}$$

wherein,
LP=−1.228−0.041*miR4732−0.066*miR22−0.02*miR30b+0.081*miR16−0.053*miR148a+0.012*miR192−0.009*miR150p−0.055*miR215+0.0899*miR486

The obtained result (Pr(cardiotoxicity)) is the expected probability of cardiotoxicity.

The miR92b-3p is used intrinsically in the equation, since it was the miRNA that was used to normalize the values of the rest of miRNAs obtained by qPCR. This miRNA is appropriate for the normalization, according to qPCR method specifications for miRNAs amplification.

The combination of the 10 miRNAs is valid to predict cardiotoxicity risk both before or once the chemotherapy has been initiated.

For the purposes of the invention, the determination of the miRNAs expression levels could be carried out by different techniques of Molecular Biology, for example qPCR or any other alternative technique generally used in the state of the art.

In a preferred embodiment, the biological sample isolated from the sample is a liquid biopsy (serum, plasma, orine, blood, etc). In a more preferred embodiment, the liquid biopsy is serum.

In a particular embodiment, the patient receiving, or susceptible to receive, anthracyclines chemotherapy is a breast cancer patient.

The modulation of the expression of the miRNAs included in the miRNA signature of the present invention result in a cardioprotection effect of cardiomyocyte cells. Accordingly, in another main aspect, the present invention refers to a method for the prevention of cardiotoxicity, in patients receiving or susceptible to receive anthracyclines chemotherapy, that comprises modulating the expression levels of the set of 10 circulating miRNAS consisting of miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p.

EXAMPLES

Materials and Methods

The study was carried out according to the principles of the Declaration of Helsinki. The researchers assured that the privacy of the patients is guaranteed. All procedures were approved by local and national ethical committees. Written informed consent was obtained from each patient.

Study Design
Prospective Observational Study
Study Population

Breast cancer patients post- or pre-antineoplastic treatment, >18 years old at time of inclusion.

Main Study Parameters/Endpoints

The primary endpoint is the development of cardiotoxicity, defined as the most recent clinical guidelines: The presence, in transthoracic echocardiography performed by a qualified physician of one of the following situations:

1. A reduction of Left Ventricle Ejection Fraction (LVEF) >5% to a final LVEF <55%, with symptoms of heart failure.

or

2. A reduction of LVEF >10% to a final LVEF <55, without the presence of symptoms.

Patients

The study population included 137 patients with different types of breast cancer that were going to receive anthracyclines. The number of positive cases of acute cardiotoxicity was 10.2%. The period for inclusion of patients was 3 years. The follow-up duration was 2 years.

The study population consisted of HER2-negative and HER2-positive breast cancer patients (n=137). These patients were scheduled to undergo different adjuvant therapies as indicated:

1) TAC chemotherapy consisted in Docetaxel 75 mg/m², Doxorubicin (Adriamycin) 50 mg/m² and Cyclophosphamide 500 mg/m², cycled every 21 day for 6 cycles (N=22).

2) AC chemotherapy consisted in Doxorubicin (adriamycin) 60 mg/m² and Cyclophosphamide 600 mg/m² cycled every 21 days for 4 cycles and then Paclitaxel (80 mg/m²) or Docetaxel (100 mg/m²) weekly for 12 weeks or cycled every 21 days for 4 cycles respectively (N=90).

3) CAELIX chemotherapy, the same treatment that AC chemotherapy but with Liposomal doxorubicin (Caelix) instead Doxorubicin (adriamycin) (N=15).

4) FEC (5-fluorouracil, epirubicin, and cyclophosphamide) (N=3)

5) Taxanes (N=7)

Clinical Data Collection

Clinical data was collected before and after receiving antineoplastic treatment. Data include demographics, medical history, cardiovascular risk factors, use of concomitant medication and/or antineoplastic regimens, symptoms and signs of cardiovascular disease, results of physical examination, echocardiography and routine laboratory results.

Serum Sample Collection

Blood samples were taken before chemotherapy directly before infusion and after completion of treatment in non-heparinized tubes. After two hours clotting, serum was harvested and stored at the Biobank of Hospital La Fe.

RNA Extraction miRNA isolation was performed used miRNeasy® kit (Qiagen, Inc.) according to the manufacture's instruction. Serum samples were thawed on ice and centrifuged for 10 min at 10,000 g 4° C. The supernatant of serum was added to QIAzol™ (Qiagen, Inc.) lysis reagent containing MS2 RNA and a known number of copies of cel-miR-39 as internal control. After vortex the mix, chloroform was added, and samples were incubated at room temperature for 5 min. Tubes were centrifuged for 15 min at 12,000 g at 4° C. 420 µl from the aqueous phase obtained after centrifugation was mixed with 280 µl of 100% ethanol. This mixture was loaded into an RNeasy® minElute™ (Qiagen, Inc.) spin column in a 2 mL collection tube and followed by centrifugation. The column was sequentially washed with Buffer RWT (700 µl) and Buffer RPE (500 µl) twice. The miRNA was eluted with 35 µl of RNase-free water.

Reverse Transcription

Reverse transcription (RT) was performed using miR-CURY LNA™ Universal RT microRNA PCR Kit (Exiqon) following manufacturer's instructions. Briefly, 2 µl of RNA was mixed with 5× Reaction Buffer (2 µl), Enzyme mix (1 µl) and nuclease free water (5 µl) to a final volume of 10 µl. The mix was incubated for 60 min at 42° C. followed by transcriptase heat-inactivation by incubating 5 min at 95° C. The product was frozen down until used.

miRNA Quantification

The quantification was performed using miRCURY LNA™ Universal RT microRNA PCR Kit and following manufacturer's instructions. Briefly, the cDNA was diluted in a 1/80 proportion in nuclease free water. 4 µl of diluted sample was mixed with 5 µl of PCR Master Mix and 1 µl of PCR primer set to a final volume of 10 µl each well. The temperature cycle program used for amplification was: 95° C. for 10 min, followed by 40 cycles at 95° C. for 15 s and 60° C. for 1 min. Real-time quantitative PCR was performed using the ViiA™ 7 Real-time PCR System (Applied Biosystems, Carlsbad, USA). Real-time monitoring of the PCR reactions was performed with the QuantStudio Real-Time PCR Software and DataAssist v3.01 (Applied Biosystems). Standard curves were made in parallel using a synthetic sequence of each miRNA. Hsa-mir-92b expression level was used as house-keeping control.

NRCMs Isolation

Neonatal rat cardiomyocytes (NRCMs) were isolated from newborn rats of 0-2 days old. Briefly, the newborn rats were euthanized by decapitation, their bodies were rinsed in ethanol 70% and the hearts were extracted in a laminar flow cabin. Hearts were minced in chunks of 1 mm³ and then incubated with trypsin at 4° C. in agitation O/N. Next day the tissue fragments were incubated with a solution of collagenase II/DNase at 37° C. 30' and then were filtered through a 40 µM cell strainer to collect the cells. Cells were preplated for 2 h to purify the cardiomyocytes and then plated at a density of 150000 cells/cm². The NRCMs were maintained in Dulbecco's Modified Eagle Medium (DMEM) High Glucose (Gibco-Invitrogen®) supplemented with 10% fetal bovine serum (FBS, Gibco-Invitrogen®), ciprofloxacin (MERCK), sodium pyruvate (MERCK) and L-glutamine (Gibco-Invitrogen®).

Cell Transfection and DOX Treatment

NRCMs were transfected using Lipofectamine® 3000 (ThermoFisher) according with manufacturer's protocol. We prepared Lipofectamine® 3000 and the Mimic separately in OptiMem™ (ThermoFisher), then mixed and incubated 15' at room temperature. Finally, we added the transfection complexes to the NRCMs and incubated for 24 h. We treated the NRCMs with doxorubicin for 24 h with Doxorubicin 1 µM after cell transfection.

Ischemia-Reperfusion Injury Model In Vitro

An oxygen and glucose deprivation (OGD) protocol was established in our laboratory to mimic I/R-induced injury in vitro. NRCMs were incubated in none glucose DMEM (Gibco®) supplied with 1% of antibiotic mixture containing P/St (Sigma-Aldrich®) and submitted to a 1% 02 and 5% $CO_2$ environment in a humidified incubator at 37° C. for 7 h (Ischemia, I). Reperfusion (R) was induced by subsequent incubation of cells with full high glucose DMEM medium (Gibco®) in 21% $O_2$ and 5% $CO_2$ atmosphere at 37° C. for 1 h. Cells cultured in normoxia (Nx) with full high glucose DMEM medium were used as control.

Cell Viability Assay

In order to evaluate the viability of the NRCMs after the treatments, we used the Cell Counting Kit 8 (CCK8, MERCK) assay following the manufacturer's instructions. The optical density of the cultures was measured at 450 nm in each well 4 h after incubation with the CCK8 assay solution.

Annexin-V Staining

To determine the percentage of apoptotic cells in the NRCMs, we performed an Annexin-V staining using the FITC Annexin V Apoptosis Detection Kit (BD Pharmingen). After the treatments the NRCMs were stained with Annexin-V and then analyze by flow cytometry.

Reactive Oxygen Species (ROS) Measurement

Oxidative stress was measured using CellROX® Orange Reagent (C10443, Molecular Probes). Briefly, NRCMs were submitted to I/R protocol as described before and incubated with CellROX® Orange Reagent solution and Hoescht33342 (1:2000, Thermo Scientific®). Live cells were visualised by In Cell Analyzer 2200 (GE Healthcare, UK) and orange intensity per cell was quantified with IN CELL Developer Tool software.

Echocardiography

Echocardiography was performed before and after the complete chemotherapeutic regime, and at 12 and 24 months after the end of the treatment. Conventional echocardiography consisted of two dimensional, and Doppler blood flow measurements to assess left ventricle (LV) structure and global function. All measurements were taken in accordance with the current guidelines of the American Society of Echocardiography using the iE33 (Philips Medical Systems, Andover, MA, USA) with transthoracic S5-1 and X5-1 broadband transducers (frequency=1-5 MHz). Digital echocardiographic data were acquired during passively held end-expiration for offline analysis using a dedicated software. Parasternal long axis view was used to measure septal and posterior wall thickness and LV systolic and diastolic diameters. Cross-sectional images were recorded from the apex, and end-diastolic and end-systolic areas and LV lengths were measured from the apical four-chamber (A4C) and two-chamber (A2C) views (using the modified biplane Simpson's method) for the calculation of ejection fraction. The mitral flow velocity was measured by pulsed wave Doppler obtained in A4C view, with the sample volume positioned at the tips of the mitral valve leaflets. Peak early diastolic velocity—E wave, peak late diastolic velocity-A wave and E/A were calculated. All tracings were made by a single observer at a centralized reading center who was blinded to all other clinical or biomarker data.

Interactome Analysis

Functional blocks from Go biological process are used in this analysis. The tables below show the count of functional classes enriched in each of the comparisons and using each of the two databases. A significance level of 0.05 was used (ie. functional blocks are called enriched if their corrected p-value is smaller than 0.05). Enriched functional blocks are classified into:
- up-regulated in the first biological condition compared to the second one
- down-regulated in the first biological condition compared to the second one, and
- not enriched.

The case of the GO database is special in that the functions or blocks of genes are organized into a directed acyclic graph (DAG) structure (en.wikipedia.org/wiki/Directed acyclic graph). This makes many of the significantly enriched functions to be redundant among them. In the second table of results of the functional profiling using the GO database we display just the significant and non redundant terms (functions); That is, the more specific terms among the significant ones.

Statistical Analysis

Since the analysis of RNAseq data can be very sensitive to the modelling decisions taken at each step, three different methods were employed to search for differentially expressed genes between positive and negative patients: Robinson and Smyth exact negative binomial test, Random Forest test and Elastic net test. The results of this analyses produced the list of miRNAs able to predict risk to suffer cardiac dysfunction after completion of chemotherapy. To develop a predictive algorithm for cardiotoxicity risk, a logistic mixed effects model considering the different previously selected miRNA as potential fixed effects predictors and the individuals as a random factor was adjusted. Variable selection was performed using Akaike's Information Criterion (AIC), selecting the model with the lowest AIC. Performance of the final model was assessed by estimating the Area under the ROC curve (AUC) and also a bootstrapped optimism-corrected version of it. P values <0.05 were considered statistically significant.

All statistical analyses were performed using R (version 3.3.1) and R-packages randomForest (version 4.6-12), glmnet (version 2.0-10), NBPSeq (version 0.3.0), lme4 (version 1.1-12) and rms (version 4.5-0).

Results

Cardiac function in terms of left ventricular ejection fraction (LVEF) in a cohort of 137 breast cancer patients receiving anthracycline chemotherapy were analyzed. Demographic data is shown in Table 1. From this cohort, 37 were discarded by uncomplete data or sample collection.

TABLE 1

Clinical characteristics of the study population

| | Controls | Cases |
|---|---|---|
| Demographics | | |
| Age (years) | 54.75 ± 12.42 (35-76) | 53.46 ± 15.71 (37-69) |
| Sex (% female) | 85 (100) | 15 (100) |
| BMI | 26.43 ± 5.16 | 26.09 ± 5.41 |
| Medical History | | |
| Hipertension (%) | 16 (18.8%) | 1 (6.6%) |
| Diabetes mellitus (%) | 6 (7.0%) | 2 (13.3%) |
| Dislipemy (%) | 31 (36.4%) | 3 (20.0%) |
| Smoking (%) | 13 (15.3%) | 2 (20%) |
| Histological subtype of cancer | | |
| Triple Negative | 14 (16.5%) | 4 (26.5%) |
| Luminal A | 5 (5.9%) | 1 (6.6%) |
| Luminal B | 9 (10.6%) | 2 (13.3) |
| HER2/Neu | 5 (5.9%) | 3 (20%) |
| Medication and cumulative dose | | |
| Taxanes | 615 ± 285 | — |
| TAC | 491.34 ± 13.19 | 465.33 ± 70.81 |
| AC | 390.52 ± 9.81n | 366.40 ± 20.61 |

From the final cohort (n=100), hematological parameters and serum biomarkers were determined before (Pre), after the last cycle of chemotherapy (Post) and one year after completion of chemotherapy (Rev), and the results are shown in Tables 2 and 3.

TABLE 2

Hematologic parameters

| | | | Pre | Post | Rev |
|---|---|---|---|---|---|
| White blood cells | Leucocytes ($10^3/\mu l$) | Control | 6.64 ± 2.14 | 5.39 ± 0.19 | 5.48 ± 0.68 |
| | | Cases | 6.36 ± 1.81 | 5.62 ± 1.04 | 5.53 ± 0.77 |
| | Neutrophils ($10^3/\mu l$) | Control | 3.85 ± 1.87 | 1.40 ± 0.06* | 3.2 ± 0.8 |
| | | Cases | 3.80 ± 1.60 | 1.29 ± 0.17* | 3.29 ± 0.9 |
| | Lymphocytes ($10^3/\mu l$) | Control | 2.09 ± 0.70 | 3.29 ± 0.18 | 1.93 ± 0.55 |
| | | Cases | 1.88 ± 0.71 | 3.41 ± 0.93* | 1.57 ± 0.48 |
| Red blood cells | Erytrocytes ($10^3/\mu l$) | Control | 4.49 ± 0.47 | 4.16 ± 0.05 | 4.29 ± 0.14 |
| | | Cases | 4.20 ± 0.50 | 4.12 ± 0.15 | 4.45 ± 0.40 |

TABLE 3

Serum biomarkers

| | | Pre | Post | Rev |
|---|---|---|---|---|
| Cholesterol | Control | 216.68 ± 3.81 | 223.23 ± 4.50 | 205.7 ± 51.90 |
| | Cases | 219.17 ± 13.43 | 214.80 ± 28.01 | 201.5 ± 52.69 |
| Triglicerides | Control | 104.16 ± 5.30 | 148.77 ± 13.96* | 117.09 ± 18.82 |
| | Cases | 78.17 ± 3.42 | 100 ± 21.33 | 93.00 ± 22.60 |
| Glucose | Control | 103.86 ± 3.50 | 97.32 ± 2.20 | 113.45 ± 10.73 |
| | Cases | 101.51 ± 2.64 | 121.33 ± 16.18 | 95.33 ± 4.70 |
| Creatinin | Control | 0.67 ± 0.01 | 0.64 ± 0.01 | |
| | Cases | 0.64 ± 0.03 | 0.56 ± 0.02 | |
| usTnT | Control | 4.27 ± 0.0.32 | 14.39 ± 0.98** | |
| | Cases | 4.47 ± 0.38 | 11.17 ± 1.80** | |

Cardiac function was monitored in these patients at these three timepoints (Pre, Pst, Rev) and, in some patients, a decline in LVEF and left ventricular end-dyastolic diameter (LVEDD) to pathological levels, as defined for cardiotoxicity in the clinical guidelines, was observed (table 4).

TABLE 4

Cardiac function parameters

| Cardiac function parameters | | Pre | Post | Rev |
|---|---|---|---|---|
| LVEF (%) | Control | 65.86 ± 6.15 | 63.30 ± 7.75 | 63.38 ± 5.94 |
| | Cases | 63.31 ± 7.87 | 56.56 ± 12.38* | 48.20 ± 8.81*** |
| LVEDD (%) | Control | 43.28 ± 0.51 | 42.67 ± 0.50 | 43.99 ± 0.58 |
| | Cases | 42.44 ± 2.39 | 46.62 ± 2.00 | 43.60 ± 2.25 |

LVEF: left ventricular ejection fraction;
LVEDD: left ventricular end diastolic diameter Among them, 10 patients that suffered cardiotoxicity during treatment defined as a decrease in 10% of FEVI below 55% (cases) were selected, and 10 additional matched patients with no affectation of cardiac function (controls). Next miRNAseq analysis using Illumina platform were performed and 200 miRNAs were detected and normalized by relative abundance.

Using three regression models, Random Forest, Negative Binomial and Elastic Net, the most differentially expressed miRNAs (n=10) between cases and controls were selected.

The random forest model achieved a cross-validated accuracy of 100% (100% sensitivity and 100% sensibility). It selected 18 miRs as the most important predictors for discriminating both groups. The Robinson and Smyth exact negative binomial test found significant differences between both groups in four miRs, three of them also present in the 18 miRs selected by random forest. Elastic net selected 16 miRs. Two of them were included in the 18 selected by the random forest model and, of those, one was also included in the 4 selected by the Robinson and Smyth test. A Venn diagram is provided to visualize the combined results of the three modeling approaches (FIG. 1). One miR has been selected by the three methods (hsa-miR-4732-3p), two have been selected by random forest and the exact negative binomial test (hsa-miR-150-5p and hsa-miR-215-5p/192-5p) and another has been selected by elastic net and random forest (hsa-miR-92b-3p). The rest of the selected miRs are the following: only selected by Robinson and Smyth exact negative binomial test: hsa-miR-148a-3p; only selected by Random Forest: hsa-miR-16-5p, hsa-miR-22-3p, 25-3p, hsa-miR-26a-5p, hsa-miR-423-5p, hsa-miR-451a, hsa-miR-486-3p/486-5p, hsa-miR-92b-3p, among others; only selected by Elastic Net: hsa-miR-30b-5p/30c-5p, among others.

Figure 2A:
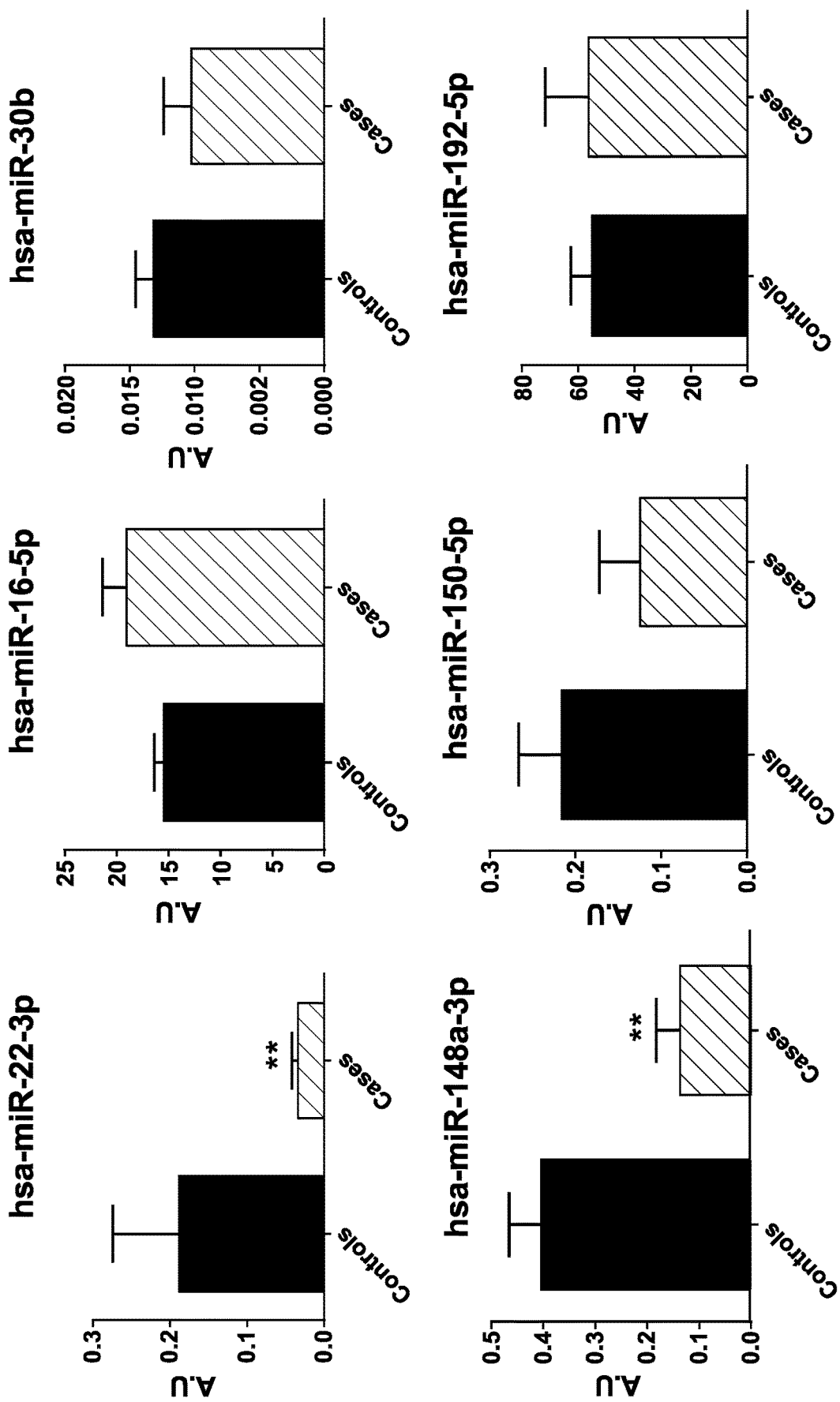
FIG. 2 (A, B). Graphics showing relative values of the 10 miRNAs (miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p) in controls and cases (N=100) as detected by qPCR. Results are expressed as mean±SEM. A.U. stands for arbitrary units. * P<0.05.
Figure 2B:
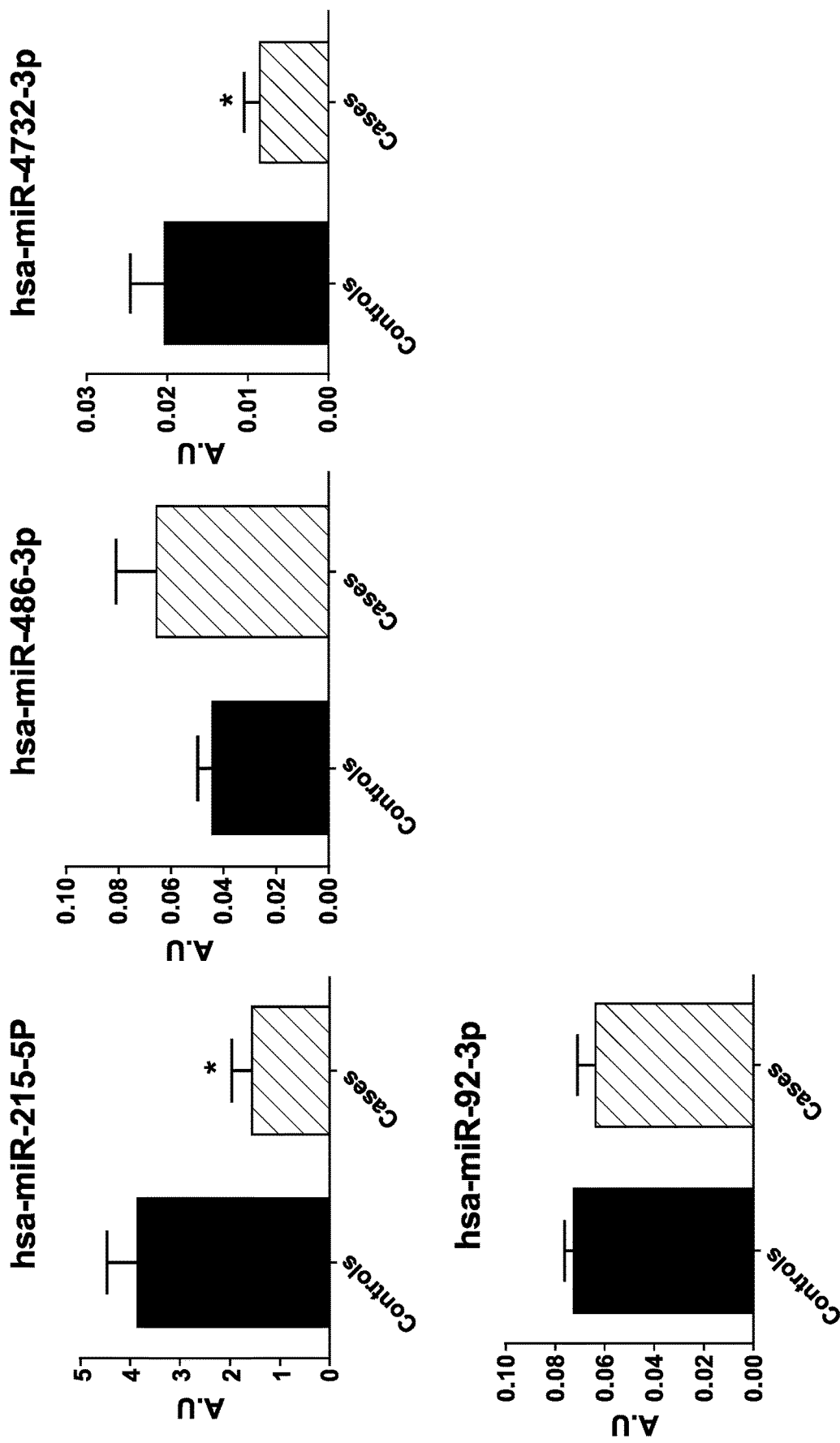
Figures 3A, 3B:
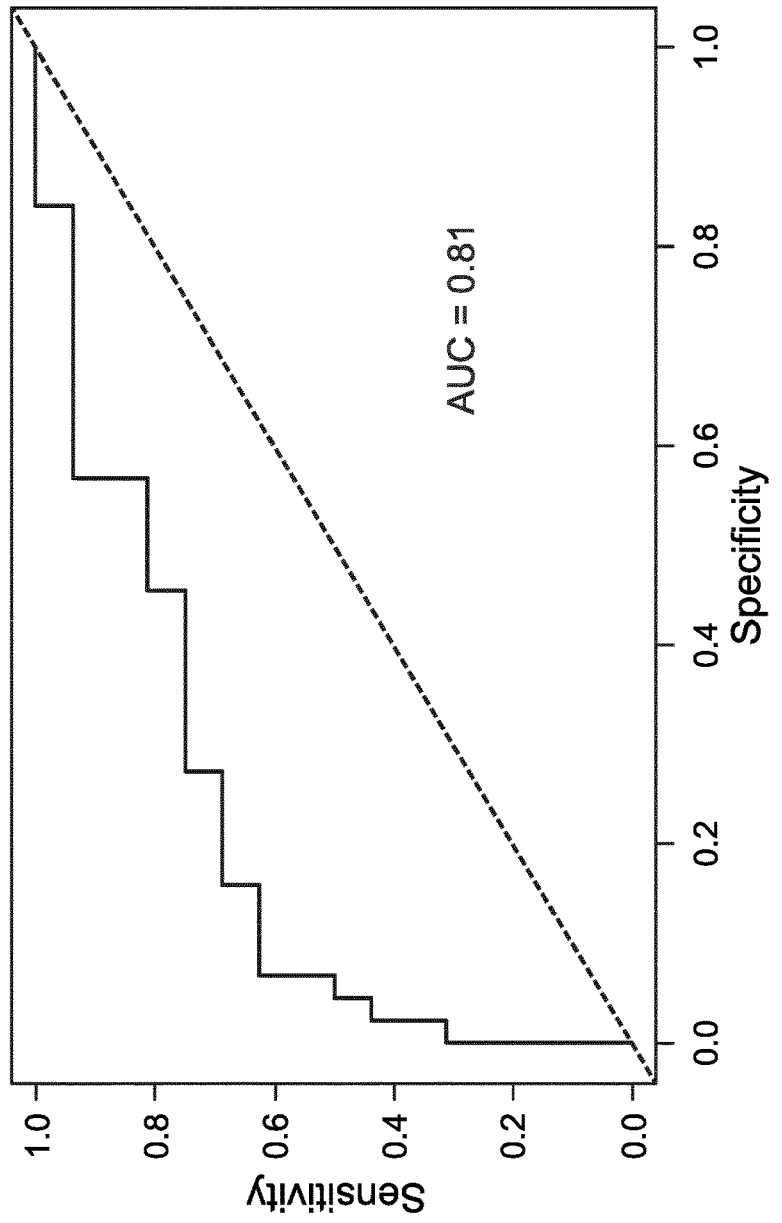
FIG. 3. (A) Determination of probability of developing cardiotoxicity (positive result) using a beta mixed model assessing the association between left ventricular ejection fraction (LVEF) and the miRNA included in MirCaTox. (B) Area under the ROC curve (AUC) showing sensitivity and specificity of the model.

Next, the expression of the 10 most significant miRNAs out of 23 miRNAs was validated (called the MirCaTox signature), in the final cohort by qPCR including the patients used in the RNAseq study. Relative values of miRNA 16-5p, miRNA 22-3p, miRNA 30b-5p/30c-5p, miRNA 92b-3p, miRNA 148a-3p, miRNA-150-5p, miRNA-192-5p, miRNA 215-5p, miRNA 486-3p/486-5p and miRNA-4732-3p were normalized to the expression of miRNA 92b-3p as described in Materials and Methods section (FIG. 2). The demographic data and clinical characteristics of the final cohort resembled the previously selected cases and controls for the RNAseq study. As expected, there was a correlation between the RNAseq and qPCR. Both techniques detected a differential expression in miRNAs defined in MirCaTox between cases and control.

Verified levels of these miRNAs were used to build a predictive model of cardiotoxic risk using a logistic mixed effects regression model. An example of algorithm using this set of miRNAs for predicting cardiotoxic risk is represented below by the following equation:

$$Pr(\text{Cardiotoxicity}) = \frac{e^{LP}}{1+e^{LP}}$$

Where

LP=−1.228−0.041*miR4732−0.066*miR22−0.02*miR30b+0.081*miR16−0.053*miR148a+0.012*miR192−0.009*miR150p−0.055*miR215+0.0899*miR486

| | | | |
|---|---|---|---|
| GO:0033260 | 0.802 | 0.006 | nuclear cell cycle DNA replication |
| GO:0046112 | 0.848 | 0.006 | nucleobase biosynthetic process |
| GO:0044272 | 0.474 | 0.007 | sulfur compound biosynthetic process |
| GO:0090002 | 0.32 | 0.009 | establishment of protein localization to plasma membrane |
| GO:0035137 | 0.808 | 0.009 | hindlimb morphogenesis |
| GO:0060020 | 0.984 | 0.009 | Bergmann glial cell differentiation |
| GO:0051188 | 0.432 | 0.009 | cofactor biosynthetic process |
| GO:0050818 | 0.484 | 0.009 | regulation of coagulation |
| GO:0021697 | 0.796 | 0.01 | cerebellar cortex formation |
| GO:0051291 | −0.335 | 0.01 | protein heterooligomerization |
| GO:0045815 | −0.353 | 0.01 | positive regulation of gene expression, epigenetic |
| GO:0006323 | −0.254 | 0.009 | DNA packaging |
| GO:0002244 | −0.328 | 0.009 | hematopoietic progenitor cell differentiation |
| GO:0043201 | −1.041 | 0.009 | response to leucine |
| GO:0050728 | −0.491 | 0.008 | negative regulation of inflammatory response |
| GO:2000756 | −0.482 | 0.008 | regulation of peptidyl-lysine acetylation |
| GO:0032438 | −0.984 | 0.008 | melanosome organization |
| GO:0009749 | −0.351 | 0.008 | response to glucose |
| GO:0072576 | −0.888 | 0.008 | liver morphogenesis |
| GO:0071103 | −0.217 | 0.007 | DNA conformation change |
| GO:0019083 | −0.241 | 0.007 | viral transcription |
| GO:0006342 | −0.324 | 0.007 | chromatin silencing |
| GO:0006336 | −0.491 | 0.007 | DNA replication-independent nucleosome assembly |
| GO:0055075 | −1.073 | 0.007 | potassium ion homeostasis |
| GO:0019080 | −0.235 | 0.007 | viral gene expression |
| GO:0031050 | −0.625 | 0.007 | dsRNA fragmentation |
| GO:0070918 | −0.625 | 0.007 | production of small RNA involved in gene silencing by RNA |
| GO:0040016 | −1.025 | 0.007 | embryonic cleavage |
| GO:0009746 | −0.353 | 0.007 | response to hexose |
| GO:0034724 | −0.487 | 0.007 | DNA replication-independent nucleosome organization |
| GO:0002440 | −0.38 | 0.007 | production of molecular mediator of immune response |
| GO:0000338 | −0.892 | 0.006 | protein deneddylation |
| GO:1903307 | −1.008 | 0.006 | positive regulation of regulated secretory pathway |
| GO:0006414 | −0.279 | 0.006 | translational elongation |
| GO:0001974 | −0.723 | 0.006 | blood vessel remodeling |
| GO:0002700 | −0.481 | 0.006 | regulation of production of molecular mediator of immune response |
| GO:0006406 | −0.353 | 0.006 | mRNA export from nucleus |
| GO:0065005 | −1.067 | 0.005 | protein-lipid complex assembly |
| GO:0006497 | −0.549 | 0.005 | protein lipidation |
| GO:0002697 | −0.271 | 0.005 | regulation of immune effector process |
| GO:0019058 | −0.181 | 0.005 | viral life cycle |
| GO:0044033 | −0.234 | 0.005 | multi-organism metabolic process |
| GO:0000183 | −0.619 | 0.005 | chromatin silencing at rDNA |
| GO:0050434 | −0.539 | 0.005 | positive regulation of viral transcription |

-continued

| | | | |
|---|---|---|---|
| GO:0043486 | −0.524 | 0.004 | histone Exchange |
| GO:0002706 | −0.468 | 0.004 | regulation of lymphocyte mediated immunity |
| GO:0048385 | −1.084 | 0.004 | regulation of retinoic acid receptor signaling pathway |
| GO:0035196 | −0.686 | 0.004 | production of miRNAs involved in gene silencing by miRNA | regulation of tumor necrosis factor-mediated signalling pathway and fibroblast apoptosis were unrepressed.

Assays in Cardiomyocytes

Figure 4A:
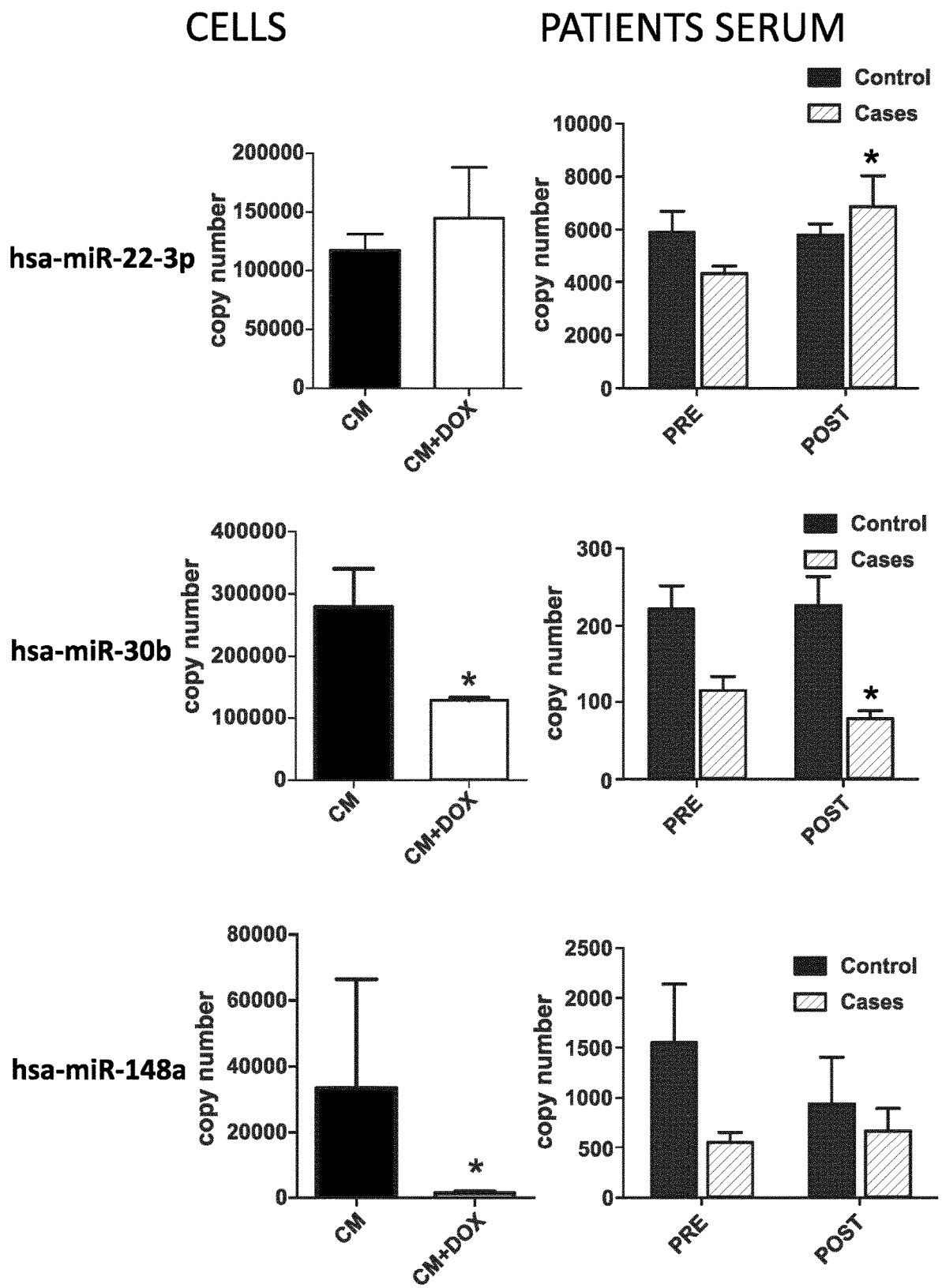
FIG. 4. (A, B) Graphics showing modulation of miRNAs by Doxorubicin in human cardiomyocytes and patients' serum. Left panels show copy number of indicated miRNAs in cardiomyocytes in culture before or after the addition of Doxorubicin (1 µM) for 24 h. Right panels show copy numbers of indicated miRNAs as detected by RNAseq in serum from control patients and cases and expressed as mean±SEM (N=10 in each case) before or after completion of anthracycline chemotherapy. Only miRNAs showing a similar tendency in cells and patients' serum are illustrated. *P<0.05.
Figure 4B:
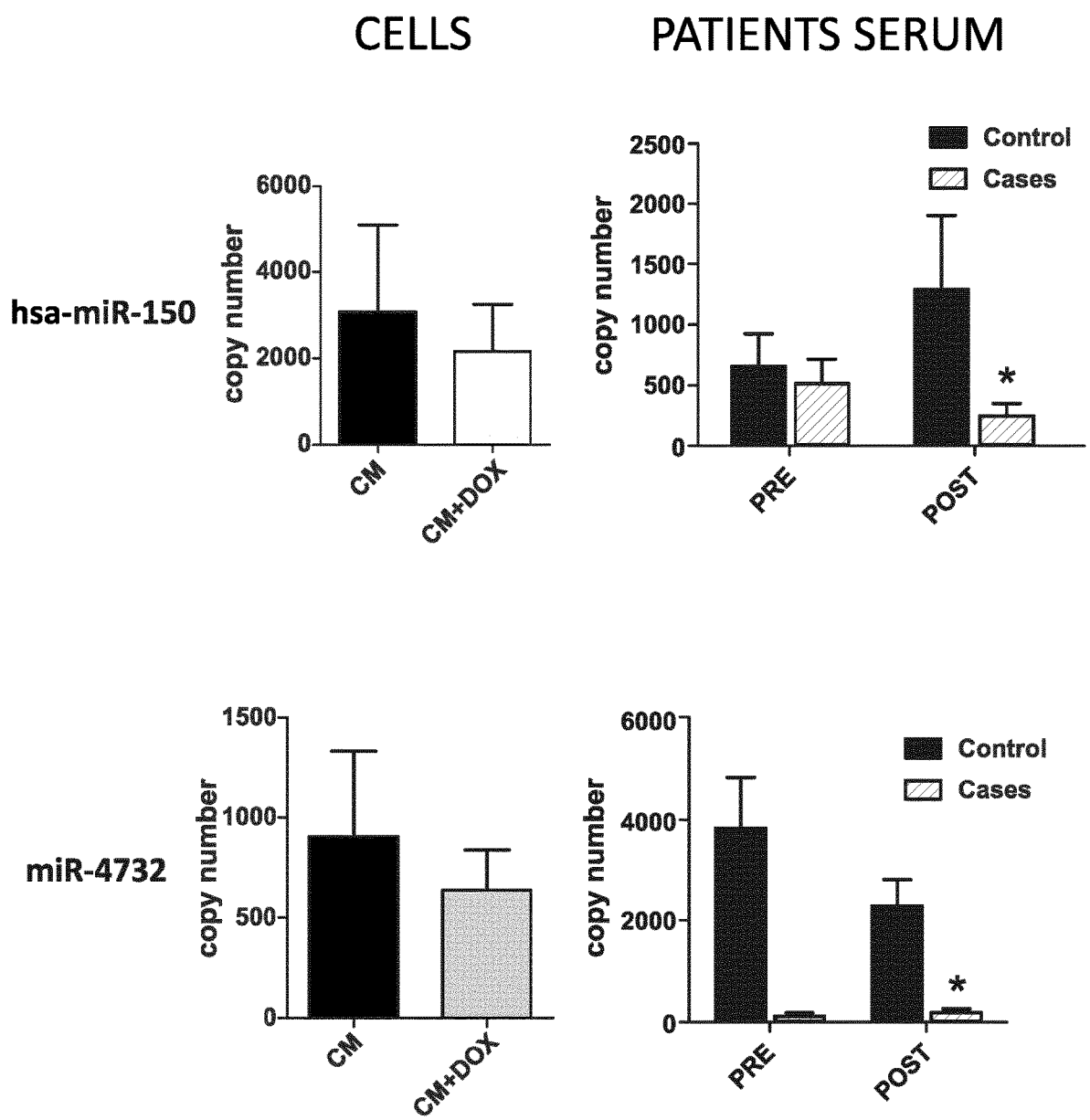
Figure 6A:
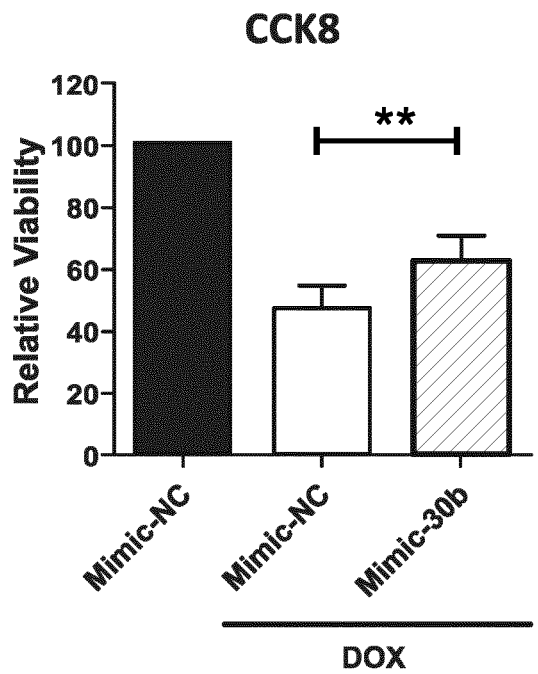
FIG. 6. Cardioprotective effects induced by overexpression of miR-30b-5p, miR-150-5p and miR-4732-3p in neonatal rat cardiomyocyte cultures (NRCMs) treated with Doxorubicin (1 µM) for 24 h in terms of cell viability (CCK8 assay) and percentage of apoptotic cells (Annexin-V positive cells). Results are expressed as mean±SEM. Cell viability is normalized to viability showed in cultures transduced with a negative control (NC) miRNA mimic and non-treated with Doxorubicin. * P<0.05, ** P<0.01
Figure 6A:
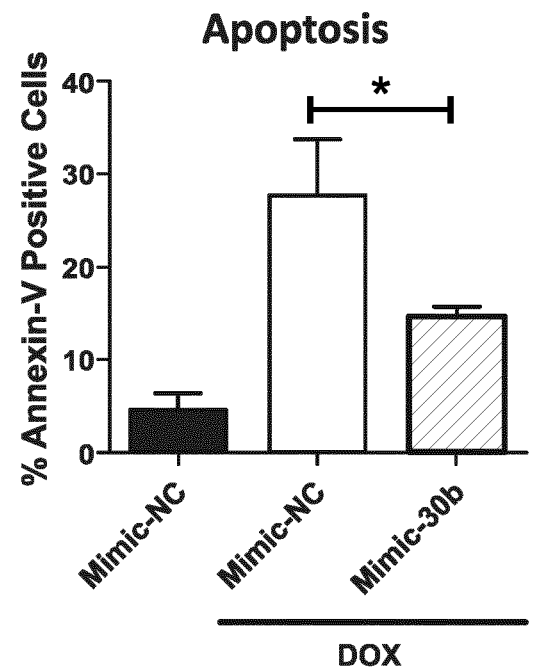
Figure 6A:
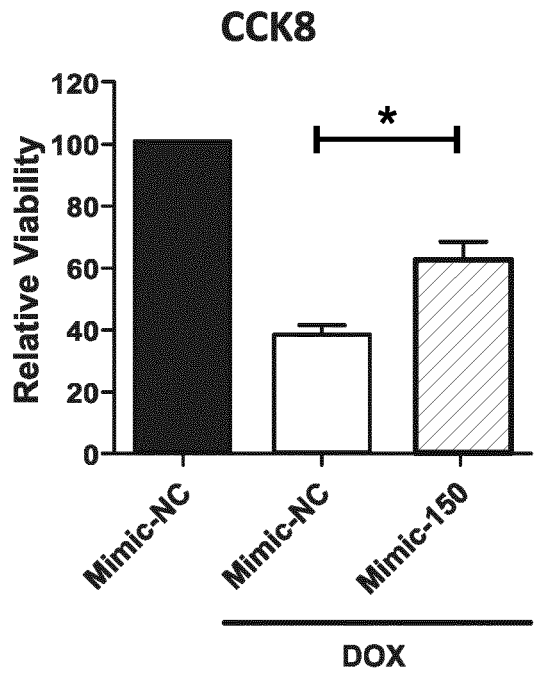
Figure 6A:
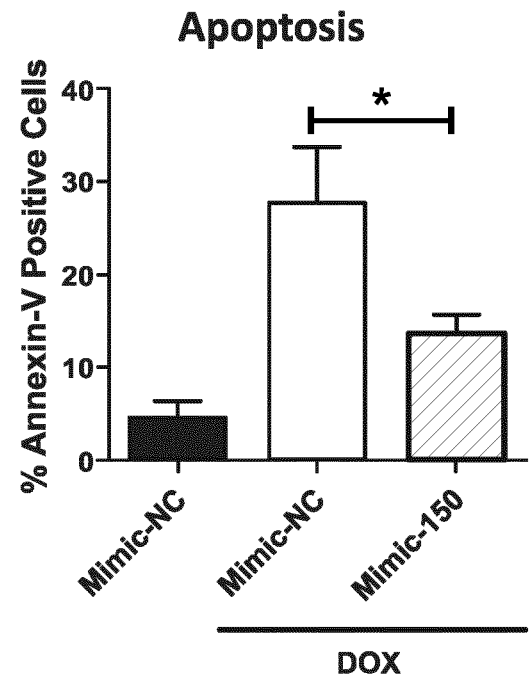
Figure 6B:
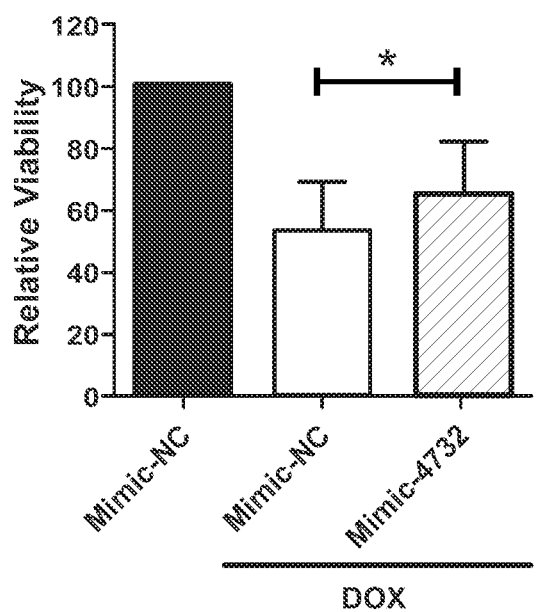
Figure 6B:
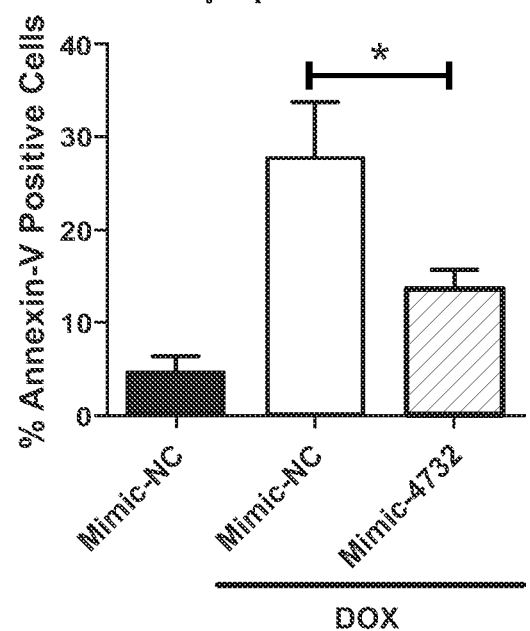

The specific signature of miRNAs has been detected in serum. Since the pathways related to miRNAs are linked to cardiomyocytes, the copy number of the miRNAs of interest in human cardiomyocytes was also measured. As observed in FIG. 4, the miRNAs previously detected in serum were also present in human cardiomyocytes (left panels) and their expression level is altered when cells are damaged by Doxorubicin. Moreover, the effect of Doxorubicin on cardiac cells resulted in similar modulation than the variation observed in patients. As shown in the right panel of FIG. 4, the copy number of miRNA-22-3p increases both in cells and serum of patients after anthracycline treatment whereas miRNA-30b, miRNA-148a, miRNA-150-5p, and miRNA-4732-3p decrease their expression levels. These results enforce the usefulness of the signature of miRNAs presented in this patent as sensor of cardiac wellness. Indeed, this set of miRNAs regulates genes involved in the aforementioned biological pathways (FIG. 5)

Figure 7:
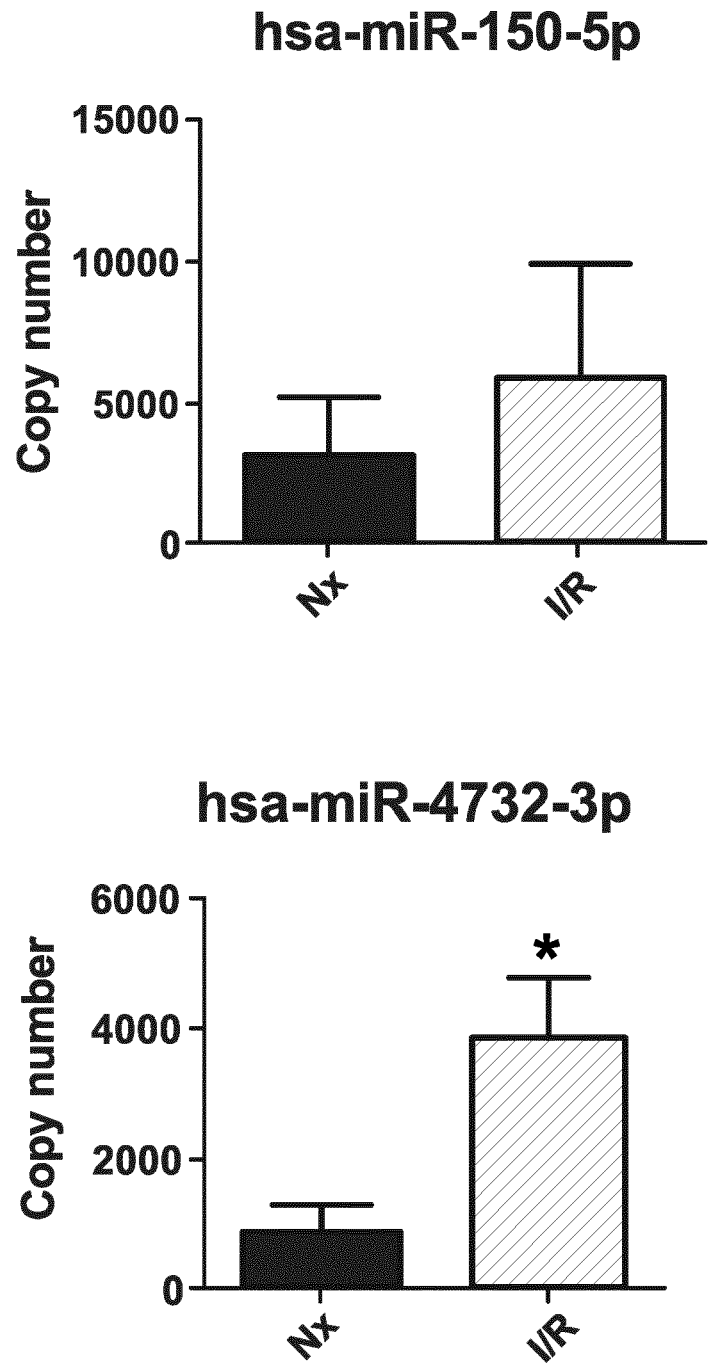
FIG. 7. Reoxygenation after ischemia modulates expression of MIRCATOX miRNAs. Effect of ischemia followed by reperfusion (I/R) in miRNA-4732-3p and miRNA-150-5p levels as quantified by qPCR. Absolute copy numbers of miRNAs are indicated in cardiomyocyte cultures treated or not with I/R culture conditions. Results are expressed as mean±SEM. * P<0.05.
Figure 8:
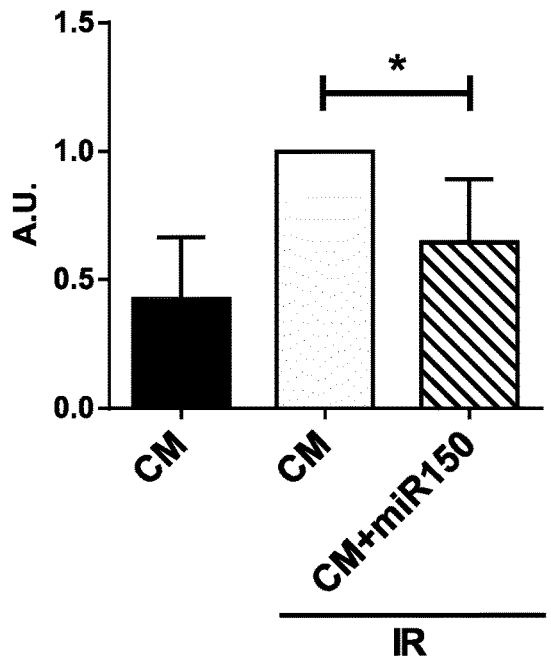
FIG. 8. Cardioprotective effects induced by overexpression of miR-150-5p and miR-4732-3p in neonatal rat cardiomyocyte cultures (NRCMs) subjected to 7 h ischemia (defined as deprivation of oxygen and nutrients) followed by 30 min reperfusion (reoxygenation and nutrient suplementation) in terms of decrease of reactive oxygen species (ROS) and apoptosis (Annexin V) in NRCMs. Results are expressed as mean±SEM. A.U. stands for arbitrary units. * P<0.05.
Figure 8:
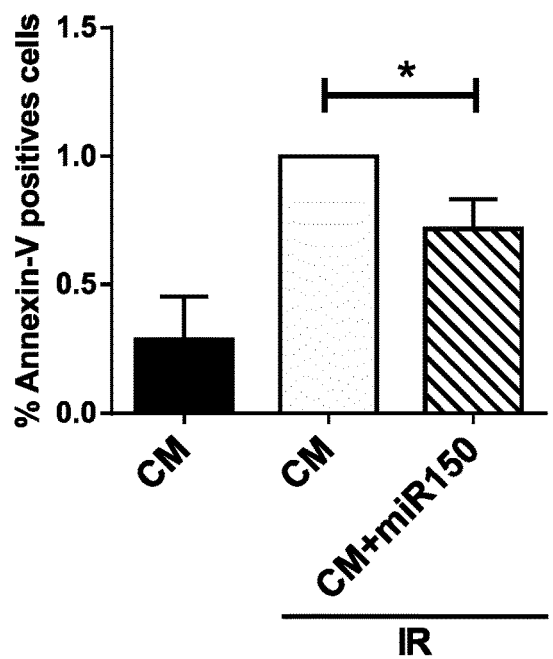
Figure 8:
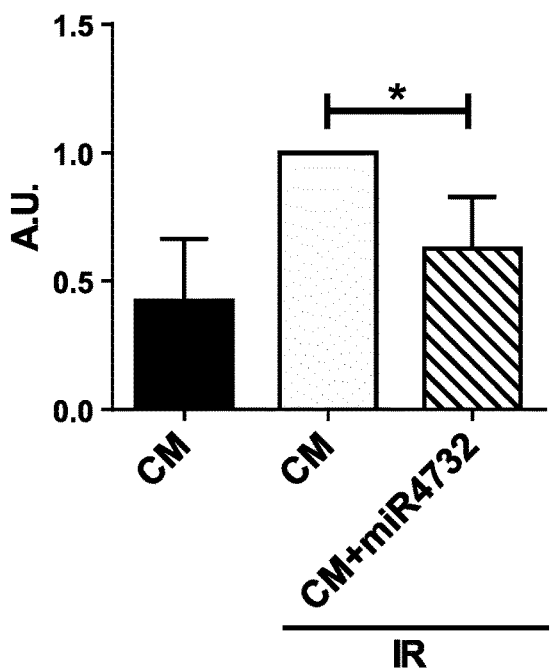
Figure 8:
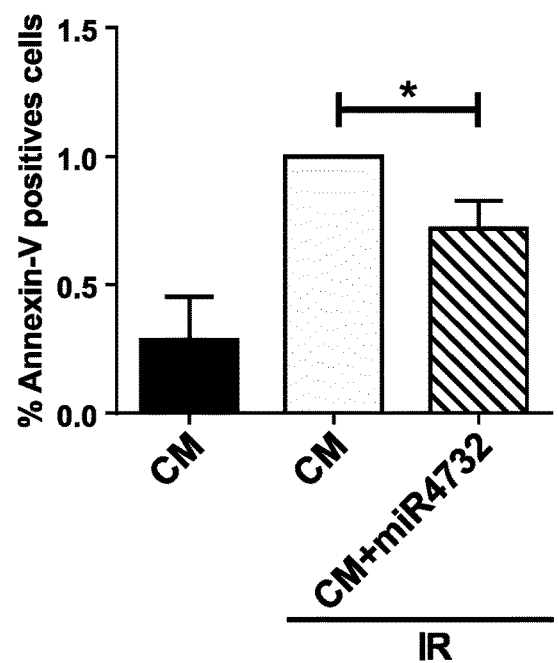

Finally, we wanted to see if modulation of miRNA levels could result in cardioprotection of cardiomyocyte cells in culture. For this purpose, we transfected NRCMs with miRNA mimics and evaluated their cardioprotective effect in terms of increase in cell viability and decrease in apoptosis in comparison to non-treated cultures after doxorubicin treatment (FIG. 6). As observed, miR-30b-5p, miR-150-5p and miR-4732-3p protected NRVCM against doxorubicin treatment. To test if cardioprotection could be extended to other types of injury we set up an in vitro experiment where cells were submmited to ischemia followed by reperfusion (I/R) as explained in materials and methods. Since reoxygenation induce both cell survival and apoptosis, we observed a strong upregulation of miR-150-5p and miR-4732 (FIG. 7), indicating that therapies aiming to modulate MirCaTox miRNAs could result in therapeutic targets to prevent cardiotoxicity. Moreover, when we performed overexpression of miR-150-5p or miR-4732-3p in NRVCM and subjected them to I/R, transfected cells showed reduced levels of ROS and apoptosis (FIG. 8).

The invention claimed is:

1. A method comprising determining the expression levels of a set of 10 circulating miRNAs in a biological sample isolated from a cancer patient, wherein the set of 10 circulating miRNAs consists of miRNA 16-5p, miRNA 22-3p, miRNA 30b-5p, miRNA 92b-3p, miRNA 148a-3p, miRNA 150-5p, miRNA 192-5p, miRNA 215-5p, miRNA 486-3p, and miRNA 4732-3p.

2. The method according to claim 1, wherein the biological sample is a liquid biopsy.

3. The method according to claim 2, wherein the liquid biopsy is serum.

4. The method according to claim 1, wherein the patient is a breast cancer patient.

* * * * *